United States Patent [19]

Gilmour

[11] 4,185,992
[45] Jan. 29, 1980

[54] IMIDAZOLE DERIVATIVES

[75] Inventor: James Gilmour, Dagenham, England

[73] Assignee: May & Baker Limited, Essex, England

[21] Appl. No.: 882,857

[22] Filed: Mar. 2, 1978

[30] Foreign Application Priority Data

Mar. 4, 1977 [GB] United Kingdom ............... 9277/77

[51] Int. Cl.$^2$ .................. C07D 233/90; A01N 9/22
[52] U.S. Cl. ........................................ 71/92; 548/343
[58] Field of Search ........................ 548/343; 71/92

[56] References Cited

U.S. PATENT DOCUMENTS

| 2,897,205 | 7/1959 | Leanza et al. | 548/343 |
| 3,886,176 | 5/1975 | Ohtsuka | 548/343 |
| 3,914,246 | 10/1975 | Baldwin et al. | 548/343 |

OTHER PUBLICATIONS

Khromov–Borisov et al. Chem. Abst. 1974, vol. 80, No. 47210k.
Vinogradova et al. Chem. Abst. 1961, vol. 55, col. 23502.
Khromov–Borisov et al. J. Org. Chem. (USSR) 1973, vol. 9, pp. 2416–2417.
Vinogradova et al. Zhur. Obshchei Khom. 1961, vol. 31, pp. 1471–1476.

*Primary Examiner*—Natalie Trousof
*Attorney, Agent, or Firm*—Stevens, Davis, Miller & Mosher

[57] ABSTRACT

Imidazole derivatives of the formula:

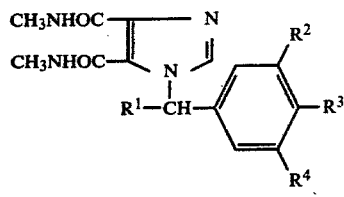

wherein $R^1$ represents hydrogen, or an alkyl group containing from 1 to 10 carbon atoms or an alkenyl or alkynyl group containing from 2 to 10 carbon atoms, and $R^2$, $R^3$ and $R^4$, which may be the same or different, each represent hydrogen, halogen or trifluoromethoxy, or a methyl, ethyl, propyl or isopropyl group optionally substituted by one or more fluorine atoms, or one of the symbols $R^2$, $R^3$ and $R^4$ represents methoxy and at least one of the other symbols $R^2$, $R^3$ and $R^4$ represents halogen or trifluoromethoxy or a methyl, ethyl, propyl or isopropyl group optionally substituted by one or more fluorine atoms, are new compounds useful as herbicides.

46 Claims, No Drawings

IMIDAZOLE DERIVATIVES

THIS INVENTION relates to new imidazole derivatives, processes for their preparation, herbicidal compositions which contain them, and their use as herbicides.

As a result of research and experimentation, it has been found that the new imidazole derivatives of the general formula:

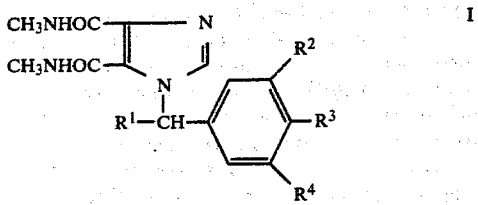

wherein $R^1$ represents a hydrogen atom or a straight- or branched-chain alkyl group containing from 1 to 10 or more usually 1 to 6 carbon atoms or a straight- or branched-chain alkenyl or alkynyl group containing from 2 to 10 carbon atoms, and $R^2$, $R^3$ and $R^4$, which may be the same or different, each represent a hydrogen or halogen (i.e. fluorine, chlorine, bromine or iodine) atom or a trifluoromethoxy group, or a methyl, ethyl, propyl or isopropyl group optionally substituted by one or more fluorine atoms, for example a trifluoromethyl group, or one of the symbols $R^2$, $R^3$ and $R^4$ represents a methoxy group and at least one of the other symbols $R^2$, $R^3$ and $R^4$ represents a halogen atom, a trifluoromethoxy group or a methyl, ethyl, propyl or isopropyl group optionally substituted by one or more fluorine atoms, possess useful herbicidal activity.

As will be apparent to those skilled in the art, compounds of general formula I may exist in optically isomeric, i.e. stereoisomeric, forms. The present invention comprises all isomeric forms of general formula I and mixtures, including racemic mixtures, thereof.

Accordingly, a feature of the present invention is a method for controlling the growth of weeds (i.e. undesired vegetation) at a locus which comprises applying to the locus a herbicidally effective amount of at least one imidazole derivative of general formula I. For this purpose, the imidazole derivatives are normally used in the form of herbicidal compositions (i.e. in association with compatible diluents or carriers suitable for use in herbicidal compositions), for example as hereinafter described.

The compounds of general formula I show herbicidal activity against monocotyledonous (e.g. grass) and dicotyledonous (i.e. broad-leafed) weeds by pre- and/or post-emergence application. By the term 'pre-emergence application' is meant application to the soil in which the weed seeds or seedlings are present before emergence of the weeds above the surface of the soil. By the term 'post-emergence application' is meant application to the aerial or exposed portions of the weeds which have emerged above the surface of the soil. For example, the compounds of general formula I may be used to control the growth of annual grass weeds, for example wild oats (*Avena* spp., e.g. *Avena fatua*), blackgrass (*Alopecurus* spp., e.g. *Alopecurus myosuroides*), foxtails (*Setaria* spp., e.g. *Setaria viridis*), barnyard grass (*Echinochloa* spp., e.g. *Echinochloa crus-galli*), Eleusine spp., e.g. *Eleusine indica*, crabgrass (*Digitaria* spp., e.g. *Digitaria sanquinalis*) and *Poa* spp., e.g. *Poa annua*, perennial grass weeds, e.g. *Agropyron repens*, *Agrostis* spp., e.g. *Agrostis stolonifera*, and *Cynodon dactylon*, annual broad leaf weeds, for example *Abutilon theophrasti*, *Amsinkia intermedia*, *Anthemis arvensis*, *Ipomea purpurea*, fathen (*Chenopodium* spp., e.g. *Chenopodium album*), pigweeds (*Amaranthus* spp., e.g. *Amaranthus retroflexus*), *Polygonum* spp., (e.g. *Polygonum lapathifolium*, *Polygonum convolvulus*, *Polygonum persicaria* and *Polygonum aviculare*), chickweeds (*Stellaria* spp., e.g. *Stellaria media*), bedstraws [*Galium* spp., e.g. cleavers (*Galium aparine*)], *Lamium* spp., e.g. *Lamium purpureum*, mayweeds (*Matricaria* spp., e.g. *Matricaria inodora*), *Portulaca* spp., e.g. *Portulaca oleracea*, *Sinapis* spp., e.g. *Sinapis arvensis*, *Raphanus raphanistrum*, *Veronica* spp., e.g. *Veronica persica* and *Veronica hederifolia*, *Chrysanthemum segetum*, *Datura stramonium*, *Descurainea sophia*, *Emex australis*, *Erysimum cheiranthoides*, *Euphorbia helioscopa*, *Galeopsis tetrahit*, *Myosotis arvensis*, *Sperqula arvensis*, *Urtica urens*, *Viola arvensis*, *Viola tricolor*, *Anagallis arvensis*, *Capsella bursa-pastoris*, *Papaver rhoeas*, *Solanum nigrum* and *Xanthium strumarium*, and perennial broad leaf weeds, for example *Rumex obtusifolius*, *Tussilago farfara* and *Cirsium arvense*, and sedges, e.g. *Cyperus rotundus*, by pre-emergence and/or post-emergence application. The compounds of general formula I also show herbicidal activity against aquatic weeds, for example *Monochoria vaginalis* and *Rotala indica*, by application to the foliage of the weeds or to the water in which they are growing and accordingly may be so-used to control the growth of those weeds.

The amounts of compounds of general formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.25 kg and 20 kg of active material per hectare give good results. However, it is to be understood that higher or lower application rates may be used, depending upon the particular problem of weed control encountered.

The compounds of general formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example graminaceous crops, e.g. wheat, barley, oats, rye, maize, rice and sorghum, soya beans, field and dwarf beans, peas, sugar beet, fodder beet and red beet, cotton, peanuts, potatoes, flax, onions, carrots, herbage seed crops and pasture, before or after sowing of the crop or before or after emergence of the crop. For the selective control of weeds at a locus of weed infestation which is an area used, or to be used, for the growing of crops, e.g. the crops hereinbefore mentioned, application rates between 0.25 kg and 8.0 kg of active material per hectare are particularly suitable.

More particularly, the compounds of general formula I, and more especially 1-(3,4-dichlorobenzyl)imidazole-N,N'-dimethyl-4,5-dicarboxamide, 1-(3,4-dibromobenzyl)imidazole-N,N'-dimethyl-4,5-dicarboxamide and 1-(4-trifluoromethylbenzyl)imidazole-N,N'-dimethyl-4,5-dicarboxamide, may be used to control selectively the growth of annual broad leaf weeds, for example to control the growth of those annual broad leaf weed species hereinbefore mentioned, by post-emergence application in a non-directional fashion, e.g. by non-directional spraying, to an area used for growing graminaceous crops, e.g. wheat, barley, oats, rye, maize, rice and sorghum, sugar beet, fodder beet, red beet, onions, herbage seed crops or pasture before or after emergence of the crop. For this purpose, i.e. the selective control of annual broad leaf weeds by post-emergence application to an area used for growing crops as immediately hereinbefore described, application rates between 0.25 kg and 4.0 kg of active material per hectare are particularly suitable.

According to a further preferred feature of the present invention, the compounds of general formula I, and more especially 1-(4-trifluoromethylbenzyl)imidazole-N,N'-dimethyl-4,5-dicarboxamide and 1-[1-(3,4-dichlorophenyl)ethyl]-imidazole-N,N'-dimethyl-4,5-dicarboxamide, may be used to control selectively the growth of annual grass and broad leaf weeds, for example to control the growth of those annual grass and broad leaf weed species hereinbefore mentioned, by pre-emergence application in a non-directional fashion, e.g. by non-directional spraying, to an area used for growing graminaceous crops, e.g. wheat, barley, oats, rye, maize, rice and sorghum and broad leaf crops, e.g. cotton, soya beans and potatoes, before the emergence of the crop above the surface of the soil. For this purpose, i.e. the selective control of annual grass and broad leaf weeds by pre-emergence application to an area used for growing crops as immediately hereinbefore described, application rates between 0.25 to 4.0 kg of active material per hectare are particularly suitable.

The compounds of general formula I, and more especially 1-(4-trifluoromethylbenzyl)imidazole-N,N'-dimethyl-4,5-dicarboxamide, 1-[1-(4-trifluoromethylphenyl)-ethyl]imidazole-N,N'-dimethyl-4,5-dicarboxamide and 1-(3,4-dichlorobenzyl)imidazole-N,N'-dimethyl-4,5-dicarboxamide, may also be used to control the growth of weeds, especially those indicated above, by pre- or post-emergence application in established orchards and other tree-growing areas, for example forests, woods and parks, plantations, e.g. sugar cane, banana, pineapple and rubber plantations, and shrubberies (including areas used for growing fruit-bearing bushes such as black-currants and red-currants). For this purpose they may be applied in a directional or non-directional fashion (e.g. by directional or non-directional spraying) to the weeds or to the soil in which they are expected to appear, before or after planting of the trees, plantations or shrubberies, at application rates between 0.25 kg and 10.0 kg of active material per hectare, and more especially in the case of sugar cane between 0.25 kg and 8.0 kg of active material per hectare (preferably between 0.25 kg and 4.0 kg of active material per hectare) for the control of annual broad leaf weeds by post-emergence application.

The compounds of general formula I may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directional fashion (e.g. by directional or non-directional spraying) at application rates between 2.0 kg and 20.0 kg of active material per hectare are particularly suitable for this purpose.

When used for the control of the growth of weeds by pre-emergence application, the compounds of general formula I may be incorporated into the soil in which the weeds are expected to emerge. It will be appreciated that when the compounds of general formula I are used to control the growth of weeds by post-emergence application, i.e. by application to the aerial or exposed portions of emerged weeds, the compounds of general formula I will also normally come into contact with the soil and may also then exercise a pre-emergence control on later-germinating weeds in the soil.

Where especially prolonged weed control is required, e.g. in loci of weed infestation which are not crop-growing areas and in plantation crops, the application of the compounds of general formula I may be repeated if required.

The utility of the compounds of general formula I as herbicides is enhanced by the fact that they are relatively harmless to mammals, demonstrated by the following test:

Mice were each treated orally with one of the compounds of general formula I, and each specific compound-dose group was observed until a period of at least three days passed without any deaths having occurred during this period.

The LD50 figures obtained (doses lethal to 50% of mice treated) are from 500 to greater than 1000 mg/kg animal body weight.

The compounds of general formula I which are preferred are those wherein $R^1$ represents a hydrogen atom or a straight-chain alkyl group containing from 1 to 8 carbon atoms, $R^2$ and $R^3$ are as hereinbefore defined and $R^4$ represents a hydrogen or chlorine atom or a trifluoromethyl group, or one of the symbols $R^2$, $R^3$ and $R^4$ represents a methoxy group and at least one of the said symbols is other than a hydrogen atom, and especially those such compounds wherein $R^1$ represents a hydrogen atom or a methyl, ethyl, propyl or butyl group, $R^2$ and $R^3$ each represents a hydrogen or halogen atom or a trifluoromethoxy, methyl, ethyl, isopropyl or trifluoromethyl group, and $R^4$ represents a hydrogen or chlorine atom or a trifluoromethyl group, or one of the symbols $R^2$, $R^3$ and $R^4$ represents a methoxy group and at least one of the said symbols is other than a hydrogen atom.

Compounds of general formula I of particular interest are 1-(4-chlorobenzyl)imidazole-N,N'-dimethyl-4,5-dicarboxamide, 1-[1-(4-chlorophenyl)ethyl]imidazole-N,N'-dimethyl-4,5-dicarboxamide, 1-[1-(4-iodophenyl)ethyl]imidazole-N,N'-dimethyl-4,5-dicarboxamide, 1-[1-(4-trifluoromethoxyphenyl)ethyl]imidazole-N,N'-dimethyl-4,5-dicarboxamide, 1-[1-(3,4-dichlorophenyl)propyl]imidazole-N,N'-dimethyl-4,5-dicarboxamide, 1-[1-(3,4-dichlorophenyl)butyl]-imidazole-N,N'-dimethyl-4,5-dicarboxamide, 1-[1-(3,4-dichlorophenyl)pentyl]imidazole-N,N'-dimethyl-4,5-dicarboxamide, 1-[1-(3,4-dibromophenyl)ethyl]imidazole-N,N'-dimethyl-4,5-dicarboxamide, 1-(4-bromo-3-chlorobenzyl)-imidazole-N,N'-dimethyl-4,5-dicarboxamide, 1-(3-chlorobenzyl)imidazole-N,N'-dimethyl-4,5-dicarboxamide, 1-[1-(3-chlorophenyl)ethyl]imidazole-N,N'-dimethyl-4,5-dicarboxamide, 1-(3-fluorobenzyl)imidazole-N,N'-dimethyl-4,5-dicarboxamide, 1-(3-trifluoromethylbenzyl)imidazole-N,N'-dimethyl-4,5-dicarboxamide, 1-[1-(3-trifluoromethylphenyl)ethyl]imidazole-N,N'-dimethyl-4,5-dicarboxamide, 1-(3,5-dichlorobenzyl)imidazole-N,N'-dimethyl-4,5-dicarboxamide, and 1-{1-[3,5-bis(trifluoromethyl)phenyl]ethyl}-imidazole-N,N'-dimethyl-4,5-dicarboxamide, and, more particularly, 1-(4-bromobenzyl)imidazole-N,N'-dimethyl4,5-dicarboxamide, 1-(4-iodobenzyl)imidazole-N,N'-dimethyl-4,5-dicarboxamide, 1-(4-trifluoromethoxybenzyl)imidazole-N,N'-dimethyl-4,5-dicarboxamide, 1-(4-trifluoromethylbenzyl)-imidazole-N,N'-dimethyl-4,5-dicarboxamide, 1-[1-(4-trifluoromethylphenyl)ethyl]imidazole-N,N'-dimethyl-4,5-dicarboxamide, 1-(3,4-dichlorobenzyl)imidazole-N,N'-dimethyl-4,5-dicarboxamide, 1-[1-(3,4-dichlorophenyl)-ethyl]imidazole-N,N'-dimethyl-4,5-dicarboxamide, 1-(3,4-dibromobenzyl)imidazole-N,N'-dimethyhl-4,5-dicarboxamide, 1-(4-chloro-3-methylbenzyl)imidazole-N,N'-dimethyl-4,5-dicarboxamide, 1-(3,4-diiodobenzyl)imidazole-N,N'-dimethyl-4,5-dicarboxamide and 1-(3,4,5-trichlorobenzyl)imidazole-N,N'-dimethyl-4,5-dicarboxamide.

Other compounds of general formula I of interest are 1-(4-fluorobenzyl)imidazole-N,N'-dimethyl-4,5-dicarboxamide, 1-(3-bromobenzyl)imidazole-N,N'-dimethyl-4,5-dicarboxamide, 1-(3-iodobenzyl)imidazole-N,N'-dimethyl-4,5-dicarboxamide, 1-(3-methylbenzyl)imidazole-N,N'-dimethyl-4,5-dicarboxamide, 1-(4-methylbenzyl)imidazole-N,N'-dimethyl-4,5-dicarboxamide, 1-(4-ethylbenzyl)-imidazole-N,N'-dimethyl-4,5-dicarboxamide, 1-(4-isopropylbenzyl)imidazole-N,N'-dimethyl-4,5-dicarboxamide, 1-(3,4-dimethylbenzyl)imidazole-N,N'-dimethyl-4,5-dicarboxamide, 1-(3-chloro-4-methoxybenzyl)imidazole-N,N'-dimethyl-4,5-dicarboxamide, 1-(3-bromo-4-methylbenzyl)-imidazole-N,N'-dimethyl-4,5-dicarboxamide, 1-(3-chloro-4-methylbenzyl)imidazole-N,N'-dimethyl-4,5-dicarboxamide, 1-[3,5-bis(trifluoromethyl)benzyl]imidazole-N,N'-dimethyl-4,5-dicarboxamide, 1-[1-(3,4-dichlorophenyl)-hexyl]imidazole-N,N'-dimethyl-4,5-dicarboxamide, 1-[1-(3,4-dichlorophenyl)-heptyl]imidazole-N,N'-dimethyl-4,5-dicarboxamide and 1-[1-(3,4-dichlorophenyl)-nonyl]imidazole-N,N'-dimethyl-4,5-dicarboxamide.

According to a feature of the present invention, the compounds of general formula I wherein $R^1$, $R^2$, $R^3$ and $R^4$ are as hereinbefore defined are prepared by the following processes:

PROCESS 1

The reaction of a compound of the general formula:

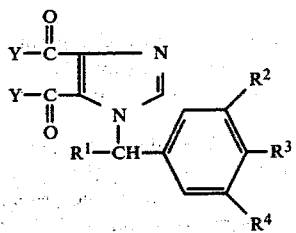

II (wherein Y represents a bromine or, preferably, chlorine atom, and $R^1$, $R^2$, $R^3$ and $R^4$ are as hereinbefore defined) with methylamine in the presence of an acid-binding agent, which is preferably an excess of methylamine, and an inert organic solvent, such as toluene, at a temperature between 0° and 30° C., and preferably at ambient temperature.

PROCESS 2

The reaction of a compound of the general formula:

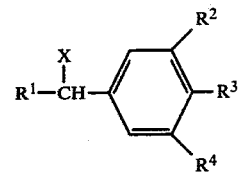

III (wherein X represents a halogen, preferably chlorine or bromine, atom, and $R^1$, $R^2$, $R^3$ and $R^4$ are as hereinbefore defined) with an alkali metal, preferably sodium, salt of imidazole-N,N'-dimethyl-4,5-dicarboxamide of the formula:

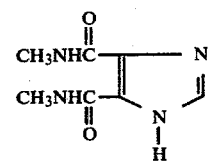

IV

The reaction may be effected in the presence of an inert organic solvent, such as dimethylformamide or t-butanol, at a temperature between 50° and 150° C., and preferably at a temperature between 60° and 110° C.

PROCESS 3

The reaction of a compound of the general formula:

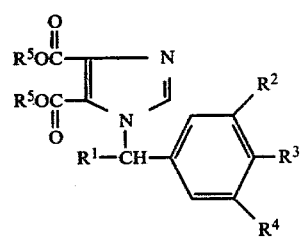

V (wherein $R^1$, $R^2$, $R^3$ and $R^4$ are as hereinbefore defined, and $R^5$ represents a straight- or branched-chain alkyl group containing from 1 to 6 carbon atoms) with methylamine in the presence of an inert organic solvent, such as toluene or ethanol, at a temperature between 0° and 100° C.

The compounds of general formula II may be prepared by the application or adaptation of known methods for the preparation of acid chlorides or bromides from carboxylic acids, for example, by the reaction of a compound of the general formula:

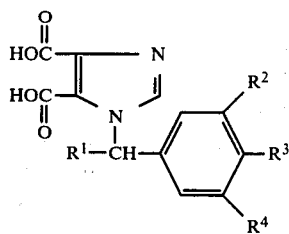

VI (wherein $R^1$, $R^2$, $R^3$ and $R^4$ are as hereinbefore defined) with thionyl chloride or bromide, and optionally with an excess of thionyl chloride or bromide.

The reaction may be effected optionally in the presence of an inert organic solvent, optionally in the presence of a catalytic amount of dimethylformamide or pyridine, at the reflux temperature of the reaction mixture.

The compounds of general formula II so obtained, after purification or without purification, may then be reacted with methylamine according to Process 1 hereinbefore described.

The compounds of general formula VI may be prepared by the application or adaptation of known methods for the preparation of carboxylic acids from nitriles, for example by the reaction of a compound of the general formula:

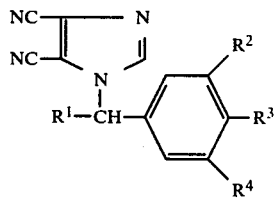

VII (wherein $R^1$, $R^2$, $R^3$ and $R^4$ are as hereinbefore defined) with an aqueous alkanolic, e.g. ethanolic, solution of an alkali metal, e.g. sodium, hydroxide at the reflux temperature of the reaction mixture.

The compounds of general formula VII may be prepared by the application or adaptation of known methods for the preparation of N-benzylimidazoles from imidazoles, for example by the reaction of an alkali metal, preferably sodium, salt of 4,5-dicyanoimidazole of the formula:

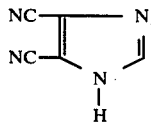

VIII with a compound of general formula III. The reaction may be effected in a manner similar to that hereinbefore described in Process 2.

Alternatively, the compounds of general formula VII may be prepared by the reaction of a compound of the general formula:

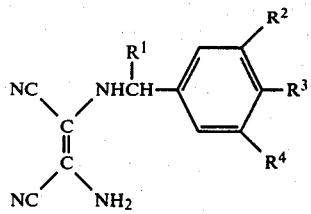

IX (wherein $R^1$, $R^2$, $R^3$ and $R^4$ are as hereinbefore defined) with (i) triethylorthoformate or (ii) formic acid.

The reaction involving triethylorthoformate may be effected in the presence of an inert organic solvent, for example ethanol, in the presence of an acidic catalyst, at a temperature between 80° and 100° C.

The reaction involving formic acid may be effected in the presence of diethyleneglycol dimethyl ether and at the reflux temperature of the reaction mixture.

The compounds of general formula IX may be prepared by the application or adaptation of known methods for the reduction of azomethines, for example by treatment of a compound of general formula:

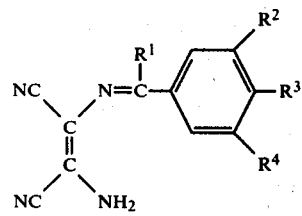

X (wherein $R^1$, $R^2$, $R^3$ and $R^4$ are as hereinbefore defined) with sodium borohydride in a mixture of methanol and tetrahydrofuran at ambient temperature.

The compounds of general formula X may be prepared by the reaction of a compound of the general formula:

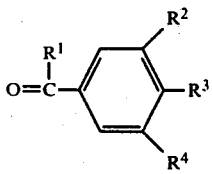

XI (wherein $R^1$, $R^2$, $R^3$ and $R^4$ are as hereinbefore defined) with diaminomaleonitrile of the formula:

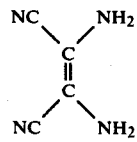

XII in the presence of an inert organic solvent, for example tetrahydrofuran or ethanol, optionally in the presence of sulphuric acid, at the reflux temperature of the reaction mixture.

The compound of formula VIII may be prepared from the compound of formula XII in a manner similar to that hereinbefore described for the preparation of the compounds of general formula VII from the compounds of general formula IX.

The compound of formula IV may be prepared by the reaction of a compound of the general formula:

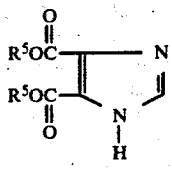

(wherein $R^5$ is as hereinbefore defined) with methylamine. The reaction may be effected in a manner similar to that hereinbefore described in Process 3.

The compounds of general formula XIV may be prepared by the reaction of the compound of formula XV with an alkanol containing from 1 to 6 carbon atoms, e.g. ethanol, in the presence of an acid catalyst, e.g. hydrogen chloride. The reaction may conveniently be effected by bubbling gaseous hydrogen chloride through an alkanolic, e.g. ethanolic, solution of the compound of formula XV at the reflux temperature of the reaction mixture.

The compounds of general formula V may be prepared by the reaction of a compound of general formula III with an alkali metal, preferably potassium, salt of a compound of general formula XIV. The reaction may be effected in a manner similar to that hereinbefore described in Process 2.

The alkali metal salts of compounds of formula IV, of formula VIII and of general formula XIV may optionally be prepared in situ, by the application or adaptation of known methods, for example the sodium salts thereof may be prepared by the reaction of compounds of formula IV, VIII and XIV with sodium hydride in the presence of dimethylformamide.

The potassium salts of compounds of general formula XIV may be prepared by the reaction of a compound of general formula XIV with potassium t-butoxide in the presence of dimethylformamide.

By the term "known methods" as used in the present specification is meant methods heretofore used or described in the chemical literature.

The following Examples and Reference Example illustrate the preparation of the compounds of the present invention.

EXAMPLE 1

1-(3,4-Dichlorobenzyl)imidazole-4,5-dicarboxylic acid (1060 g) was heated at reflux with stirring with thionyl chloride (2.5 liters) in the presence of dry dimethylformamide (5 ml) for 4 hours. The excess of thionyl chloride was removed by evaporation and final traces were removed by repeated evaporation in the presence of dry toluene (4×1.25 liters). 1-(3,4-Dichlorobenzyl)imidazole-4,5-dicarbonyl chloride, which was obtained as an orange syrup, was dissolved in dry toluene (1 liter). The solution was added over 2 hours at 0°-10° C. to a stirred saturated solution of methylamine in toluene (5 liters) whilst maintaining a flow of methylamine gas. The mixture was stirred for 6 hours at room temperature and filtered to give a white solid, which was dissolved in chloroform (2 liters). The chloroformic solution was washed with water (500 ml), dried over magnesium sulphate, filtered and evaporated to give 1-(3,4-dichlorobenzyl)imidazole-N,N'-dimethyl-4,5-dicarboxamide, a pale yellow solid, m.p. 126°-128° C. (516 g). The organic filtrate from the reaction mixture was washed with water (500 ml), dried over sodium sulphate, filtered and evaporated to give a yellow powder, which was triturated with toluene (400 ml) to give more product as a white solid, m.p. 126°-129° C. (355 g).

By proceeding in a similar manner but replacing the 1-(3,4-dichlorobenzyl)imidazole-4,5-dicarboxylic acid by the appropriately substituted imidazole-4,5-dicarboxylic acids there were prepared:

1-(3-fluorobenzyl)imidazole-N,N'-dimethyl-4,5-dicarboxamide, m.p. 103.5°-104° C. (after crystallisation from ethanol), from 1-(3-fluorobenzyl)imidazole-4,5-dicarboxylic acid;

1-(4-fluorobenzyl)imidazole-N,N'-dimethyl-4,5-dicarboxamide, m.p. 94°-95° C. (after crystallisation from hexane), from 1-(4-fluorobenzyl)imidazole-4,5-dicarboxylic acid;

1-(3-chlorobenzyl)imidazole-N,N'-dimethyl-4,5-dicarboxamide, m.p. 121°-121.5° C. (after crystallisation from ethanol), from 1-(3-chlorobenzyl)imidazole-4,5-dicarboxylic acid;

1-(4-chlorobenzyl)imidazole-N,N'-dimethyl-4,5-dicarboxamide, m.p. 131°-132° C. (after crystallisation from ethanol), from 1-(4-chlorobenzyl)imidazole-4,5-dicarboxylic acid;

1-(3-bromobenzyl)imidazole-N,N'-dimethyl-4,5-dicarboxamide, m.p. 114°-115° C., (after crystallisation from ethanol), from 1-(3-bromobenzyl)imidazole-4,5-dicarboxylic acid;

1-(4-bromobenzyl)imidazole-N,N'-dimethyl-4,5-dicarboxamide, m.p. 149°-150° C. from 1-(4-bromobenzyl)-imidazole-4,5-dicarboxylic acid;

1-(3-iodobenzyl)imidazole-N,N'-dimethyl-4,5-dicarboxamide, m.p. 112°-114° C. (after crystallisation from ethanol), from 1-(3-iodobenzyl)imidazole-4,5-dicarboxylic acid;

1-(4-iodobenzyl)imidazole-N,N'-dimethyl-4,5-dicarboxamide, m.p. 150°-151° C. (after crystallisation from ethanol), from 1-(4-iodobenzyl)imidazole-4,5-dicarboxylic acid;

1-(3,4-dibromobenzyl)imidazole-N,N'-dimethyl-4,5-dicarboxamide, m.p. 118°-119° C. (after crystallisation from ethanol), from 1-(3,4-dibromobenzyl)imidazole-4,5-dicarboxylic acid;

1-(3,5-dichlorobenzyl)imidazole-N,N'-dimethyl-4,5-dicarboxamide, m.p. 135°-136° C. (after crystallisation from ethanol) from 1-(3,5-dichlorobenzyl)imidazole-4,5-dicarboxylic acid;

1-(3-methylbenzyl)imidazole-N,N'-dimethyl-4,5-dicarboxamide, m.p. 84°-85° C. (after crystallisation from ether) from 1-(3-methylbenzyl)imidazole-4,5-dicarboxylic acid;

1-(4-methylbenzyl)imidazole-N,N'-dimethyl-4,5-dicarboxamide, m.p. 115°-116° C. (after crystallisation from aqueous ethanol), from 1-(4-methylbenzyl)imidazole-4,5-dicarboxylic acid;

1-(4-ethylbenzyl)imidazole-N,N'-dimethyl-4,5-dicarboxamide, m.p. 68°-69° C. (after crystallisation from cyclohexane), from 1-(4-ethylbenzyl)imidazole-4,5-dicarboxylic acid;

1-(4-isopropylbenzyl)imidazole-N,N'-dimethyl-4,5-dicarboxamide, m.p. 54°-56° C. (after crystallisation from hexane), from 1-(4-isopropylbenzyl)imidazole-4,5-dicarboxylic acid;

1-(3,4-dimethylbenzyl)imidazole-N,N'-dimethyl-4,5-dicarboxamide, m.p. 168°-170° C. (after crystallisation from a mixture of toluene and petroleum ether, b.p.

60°–80° C.), from 1-(3,4-dimethylbenzyl)imidazole-4,5-dicarboxylic acid;

1-(3-trifluoromethylbenzyl)imidazole-N,N'-dimethyl-4,5-dicarboxamide, m.p. 108°–110° C. (after crystallisation from a mixture of hexane and ethanol), from 1-(3-trifluoromethylbenzyl)imidazole-4,5-dicarboxylic acid;

1-(4-trifluoromethylbenzyl)imidazole-N,N'-dimethyl-4,5-dicarboxamide, m.p. 131°–132° C. (after crystallisation from cyclohexane), from 1-(4-trifluoromethylbenzyl)imidazole-4,5-dicarboxylic acid;

1-(4-trifluoromethoxybenzyl)imidazole-N,N'-dimethyl-4,5-dicarboxamide, m.p. 110.5° C. (after crystallisation from ethanol), from 1-(4-trifluoromethoxybenzyl)imidazole-4,5-dicarboxylic acid;

1-(3-chloro-4-methoxybenzyl)imidazole-N,N'-dimethyl-4,5-dicarboxamide, m.p. 122°–123° C. (after crystallisation from a mixture of toluene and cyclohexane), from 1-(3-chloro-4-methoxybenzyl)imidazole-4,5-dicarboxylic acid; and ($\pm$)-1-[1-(3,4-dichlorophenyl)ethyl]imidazole-N,N'-dimethyl-4,5-dicarboxamide, m.p. 124°–126° C. (after crystallisation from methanol), from ($\pm$)-1-[1-(3,4-dichlorophenyl)ethyl]imidazole-4,5-dicarboxylic acid.

The benzylimidazole-4,5-dicarboxylic acids used as starting materials in the above preparations were prepared as follows:

1-(3,4-Dichlorobenzyl)-4,5-dicyanoimidazole (2180 g) was heated at reflux with stirring in a solution of sodium hydroxide (1260 g) in a mixture of ethanol (5 liters) and water (4.4 liters) for 48 hours. The cooled mixture was diluted with water (20 liters), washed with diethyl ether (2 liters) and acidified with concentrated hydrochloric acid (3.5 liters) with cooling on an ice-bath. The precipitate, a pale yellow solid, was filtered off, washed with water and dissolved in portions in water (150 liters) containing sodium bicarbonate (4700 g). The solution was filtered and acidified with concentrated hydrochloric acid to give 1-(3,4-dichlorobenzyl)imidazole-4,5-dicarboxylic acid, m.p. 258° C. with decomposition, (1157 g), as an off-white powder.

By proceeding in a similar manner but replacing the 1-(3,4-dichlorobenzyl)-4,5-dicyanoimidazole by the appropriate benzyldicyanoimidazoles there were prepared:

1-(3-fluorobenzyl)imidazole-4,5-dicarboxylic acid, m.p. 224° C. with decomposition, from 1-(3-fluorobenzyl)-4,5-dicyanoimidazole;

1-(4-fluorobenzyl)imidazole-4,5-dicarboxylic acid, m.p. 248°–252° C. with decomposition, from 1-(4-fluorobenzyl)-4,5-dicyanoimidazole;

1-(3-chlorobenzyl)imidazole-4,5-dicarboxylic acid, m.p. 248°–249° C. with decomposition, from 1-(3-chlorobenzyl)-4,5-dicyanoimidazole;

1-(4-chlorobenzyl)imidazole-4,5-dicarboxylic acid, m.p. 258°–258.5° C. with decomposition, from 1-(4-chlorobenzyl)-4,5-dicyanoimidazole;

1-(3-bromobenzyl)imidazole-4,5-dicarboxylic acid, m.p. 223°–226° C. with decomposition, from 1-(3-bromobenzyl)-4,5-dicyanoimidazole;

1-(4-bromobenzyl)imidazole-4,5-dicarboxylic acid, m.p. 245°–246° C. with decomposition, from 1-(4-bromobenzyl)-4,5-dicyanoimidazole;

1-(3-iodobenzyl)imidazole-4,5-dicarboxylic acid, m.p. 211° C. with decomposition, from 1-(3-iodobenzyl)-4,5-dicyanoimidazole;

1-(4-iodobenzyl)imidazole-4,5-dicarboxylic acid, m.p. 241° C. with decomposition, from 1-(4-iodobenzyl)-4,5-dicyanoimidazole;

1-(3,4-dibromobenzyl)imidazole-4,5-dicarboxylic acid, m.p. 224° C. with decomposition, from 1-(3,4-dibromobenzyl)-4,5-dicyanoimidazole;

1-(3,5-dichlorobenzyl)imidazole-4,5-dicarboxylic acid, m.p. 267°–269° C. with decomposition, from 1-(3,5-dichlorobenzyl)-4,5-dicyanoimidazole;

1-(3-methylbenzyl)imidazole-4,5-dicarboxylic acid, m.p. 185° C. with decomposition, from 1-(3-methylbenzyl)-4,5-dicyanoimidazole;

1-(4-methylbenzyl)imidazole-4,5-dicarboxylic acid, m.p. 248°–250° C. with decomposition, from 1-(4-methylbenzyl)-4,5-dicyanoimidazole;

1-(4-ethylbenzyl)imidazole-4,5-dicarboxylic acid, m.p. 211°–212° C. with decomposition, from 1-(4-ethylbenzyl)-4,5-dicyanoimidazole;

1-(4-isopropylbenzyl)imidazole-4,5-dicarboxylic acid, m.p. 189°–191° C. with decomposition, from 1-(4-isopropylbenzyl)-4,5-dicyanoimidazole;

1-(3,4-dimethylbenzyl)imidazole-4,5-dicarboxylic acid, m.p. 258°–260° C. with decomposition, from 1-(3,4-dimethylbenzyl)-4,5-dicyanoimidazole;

1-(3-trifluoromethylbenzyl)imidazole-4,5-dicarboxylic acid, m.p. 226°–227° C. with decomposition, from 1-(3-trifluoromethylbenzyl)-4,5-dicyanoimidazole;

1-(4-trifluoromethylbenzyl)imidazole-4,5-dicarboxylic acid, m.p. 223° C. with decomposition, from 1-(4-trifluoromethylbenzyl)-4,5-dicyanoimidazole;

1-(4-trifluoromethoxybenzyl)imidazole-4,5-dicarboxylic acid, m.p. 214°–215° C. with decomposition, from 1-(4-trifluoromethoxybenzyl)-4,5-dicyanoimidazole;

1-(3-chloro-4-methoxybenzyl)imidazole-4,5-dicarboxylic acid, m.p. 223° C. with decomposition, from 1-(3-chloro-4-methoxybenzyl)-4,5-dicyanoimidazole; and ($\pm$)-1-[1-(3,4-dichlorophenyl)ethyl]imidazole-4,5-dicarboxylic acid, m.p. 169° C. with decomposition, from ($\pm$)-1-[1-(3,4-dichlorophenyl)-ethyl]-4,5-dicyanoimidazole.

The benzyldicyanoimidazoles used as starting materials in the above preparations were prepared as follows:

4,5-Dicyanoimidazole (93 g, described by Woodward, U.S. Pat. No. 2534331 (1950)) was dissolved in dry dimethylformamide (500 ml) with stirring. Sodium hydride (20 g) was added to the solution in portions at such a rate that the temperature after the addition was 90° C. When effervescence had ceased the solution was heated on a steam bath for 15 minutes and then allowed to cool to 60° C. 3,4-Dichlorobenzyl chloride (230 g, described by Beilstein & Kuhlberg, Ann., 146, 326 (1867)) was added over 30 minutes to the solution, which was heated on a steam bath for 6 hours and then at 150° C. for 10 minutes. The cooled reaction mixture was poured into water (2 liters) and a brown solid was filtered off and washed with water. The damp solid was recrystallised from ethanol (1 liter) to give 1-(3,4-dichlorobenzyl)-4,5-dicyanoimidazole, m.p. 132°–134° C., (114 g) as off-white crystals.

By proceeding in a similar manner but replacing the 3,4-dichlorobenzyl chloride by the appropriately substituted benzyl halide there were prepared:

1-(3-fluorobenzyl)-4,5-dicyanoimidazole, m.p. 97.5°–98° C. (after crystallisation from ethanol), from 3-fluorobenzyl chloride (described by Jerumanis & Bruylants, Bull. Soc. Chim. Belges, 69, 312 (1960));

1-(4-fluorobenzyl)-4,5-dicyanoimidazole, m.p. 142°–144° C. (after crystallisation from aqueous ethanol), from 4-fluorobenzyl chloride (described by Olah, Pavlath and Kuhn, Acta. Chim. Acad. Sci. Hung., 7, 85 (1955));

1-(3-chlorobenzyl)-4,5-dicyanoimidazole, m.p. 110°–111° C. (after crystallisation from aqueous ethanol), from 3-chlorobenzyl chloride (described by Franzen & Rosenberg, J. prakt. Chem., [2], 101, 334 (1867));

1-(4-chlorobenzyl)-4,5-dicyanoimidazole, m.p. 119.5°–120° C. (after crystallisation from ethanol), from 4-chlorobenzyl chloride (described by Olivier, Rec. Trav. Chim., 41, 308 (1922));

1-(3-bromobenzyl)-4,5-dicyanoimidazole, m.p. 101.5°–102.5° C. (after crystallisation from ethanol), from 3-bromobenzyl chloride (described by Olivier, Rec. Trav. Chim., 41, 649 (1922));

1-(4-bromobenzyl)-4,5-dicyanoimidazole, m.p. 118°–119° C. (after crystallisation from aqueous ethanol), from 4-bromobenzyl chloride (described by Boeseken, Rec. Trav. Chim., 23, 99 (1904));

1-(3-iodobenzyl)-4,5-dicyanoimidazole, m.p. 96°–98° C. (after crystallisation from ethanol), from 3-iodobenzyl bromide (described by Olivier, Rec. Trav. Chim., 42, 520 (1923));

1-(4-iodobenzyl-4,5-dicyanoimidazole, m.p. 111°–112° C. (after crystallisation from ethanol), from 4-iodobenzyl bromide (described by Olivier, Rec. Trav. Chim., 42, 519 (1923));

1-(3,4-dibromobenzyl)-4,5-dicyanoimidazole, m.p. 135°–138° C., from 3,4-dibromobenzyl chloride;

1-(3,5-dichlorobenzyl)-4,5-dicyanoimidazole, m.p. 134°–135.5° C. (after crystallisation from ethanol), from 3,5-dichlorobenzyl chloride [described by Fuchs and Carlton, JACS 85, 107 (1963)];

1-(3-methylbenzyl)-4,5-dicyanoimidazole, as a brown oil, which was not distilled, from 3-methylbenzyl chloride (described by Olivier, Rec. Trav. Chim., 41, 307 (1922));

1-(4-methylbenzyl)-4,5-dicyanoimidazole, m.p. 158°–161° C. (after crystallisation from aqueous ethanol), from 4-methylbenzyl chloride (described by Olivier, Rec. Trav. Chim., 41, 405 (1922));

1-(4-ethylbenzyl)-4,5-dicyanoimidazole, as a brown semi-solid, from 4-ethylbenzyl chloride (described by Blanc, Bull. Soc. Chim., [4], 33, 317 (1923));

1-(4-isopropylbenzyl)-4,5-dicyanoimidazole, as a brown oil, from 4-isopropylbenzyl chloride (described by Blanc, Bull. Soc. Chim., [4], 33, 317 (1923));

1-(3,4-dimethylbenzyl)-4,5-dicyanoimidazole, m.p. 113°–115° C. (after crystallisation from ethanol), from 3,4-dimethylbenzyl chloride (described by Sommelet, Compte Rendu, 157, 1445 (1913));

1-(3-trifluoromethylbenzyl)-4,5-dicyanoimidazole, m.p. 64°–65° C. (after crystallisation from aqueous ethanol), from 3-trifluoromethylbenzyl chloride (described by Benjamin & Percherer, U.S. Pat. No. 3,465,051 (1966));

1-(4-trifluoromethylbenzyl)-4,5-dicyanoimidazole, m.p. 101°–102° C. (after crystallisation from ethanol), from 4-trifluoromethylbenzyl chloride (described by Sarett & Shen, U.S. Pat. No. 3,196,162 (1959));

1-(4-trifluoromethoxybenzyl)-4,5-dicyanoimidazole, m.p. 62.5°–63° C. (after crystallisation from ethanol), from 4-trifluoromethoxybenzyl chloride;

1-(3-chloro-4-methoxybenzyl)-4,5-dicyanoimidazole, m.p. 144°–146° C. (after crystallisation from ethanol), from 3-chloro-4-methoxybenzyl chloride (described by Naik and Wheeler, J.C.S. 1938, 1780); and (±)-1-[1-(3,4-dichlorophenyl)ethyl]-4,5-dicyanoimidazole, m.p. 166°–168° C. (after crystallisation from toluene), from (±)-1-(3,4-dichlorophenyl)ethyl chloride (described by Manuel et al. J.A.C.S. 68, 861 (1946)).

3,4-Dibromobenzyl chloride used in one of the above preparations was made as follows:

3,4-Dibromobenzoic acid (28 g, described by Miller, J.C.S. 61, 1033 (1892)) was suspended with stirring in toluene (150 ml) at 50° C. Sodium dihydrobis(2-methoxyethoxy)aluminate (70% w/v, in toluene, 52 ml) was added over 30 minutes at 50° C. The mixture was heated on a steam bath for 1 hour, cooled to 20° C. and hydrolysed by the addition of hydrochloric acid (6N; 150 ml) with cooling. The mixture was separated and the aqueous phase was extracted with diethyl ether (100 ml). The combined organic extracts were washed with saturated sodium bicarbonate solution and water, dried over sodium sulphate, filtered and evaporated to give 3,4-dibromobenzyl alcohol (19 g) as a light red oil. The unpurified alcohol was dissolved in chloroform (60 ml) and the solution was heated at reflux. Thionyl chloride (20 ml) was added in portions over 10 minutes and the solution was heated at reflux for 1 hour. The reaction mixture was evaporated to give a light oily residue, which was repeatedly diluted with chloroform (3×50 ml) and the combined chloroformic solutions evaporated. The residue was dissolved in diethyl ether, washed with saturated sodium bicarbonate solution, dried over sodium sulphate, filtered and evaporated. 3,4-Dibromobenzyl chloride (20 g) was obtained as a clear mobile oil of sufficient purity for further reaction.

By proceeding in a similar manner but replacing the 3,4-dibromobenzoic acid by 4-trifluoromethoxybenzoic acid (described by Sheppard, J. Org. Chem., 29, 1 (1964)), 4-trifluoromethoxybenzyl chloride, also used in one of the above preparations, in the form of a clear mobile oil, was prepared.

EXAMPLE 2

A solution of diethyl 1-(3,4-dichlorobenzyl)-imidazole-4,5-dicarboxylate (0.9 g) in ethanolic methylamine (5% v/v, 12 ml) was heated in a sealed vessel at 100° C. for 24 hours. The cooled reaction mixture was diluted with water (20 ml) to precipitate 1-(3,4-dichlorobenzyl)imidazole-N,N'-dimethyl-4,5-dicarboxamide, m.p. 125°–126° C., (0.5 g) as off-white crystals.

Diethyl 1-(3,4-dichlorobenzyl)imidazole-4,5-dicarboxylate required for the above preparation was prepared as follows:

Potassium t-butoxide (10.9 g) was added with stirring to a solution of diethyl imidazole-4,5-dicarboxylate (20 g, described by Jones, J.A.C.S. 74, 1085 (1952)) in dry dimethylformamide (300 ml) at room temperature and the mixture was stirred for 40 minutes. 3,4-Dichlorobenzyl chloride (20.4 g) was added and the mixture was heated at reflux for 11 hours. The cooled reaction mixture was poured into ice-water (500 ml) and extracted with chloroform (2×200 ml). The combined extracts were washed with water (3×300 ml), dried over magnesium sulphate, filtered and evaporated to dryness. The solid residue was crystallised from methanol (100 ml) to give diethyl 1-(3,4-dichlorobenzyl)imidazole-4,5-dicarboxylate, m.p. 105°–107° C., (13 g) as a colourless solid.

EXAMPLE 3

Imidazole-N,N'-dimethyl-4,5-dicarboxamide (1.8 g; described by Vinogradova and Khromov-Borisov, Zhur. Obschii Khim., 31, 1466 (1961)) was partially dissolved in dry dimethylformamide (10 ml) with stirring. Sodium hydride (0.24 g) was added to the mixture and the temperature rose to 60° C. This temperature was maintained by external heating until complete solution was obtained (15 minutes). 3,4-Dichlorobenzyl chloride (1.95 g) was added to the solution, which was heated at 70° C. for 6 hours. The cooled reaction mixture was diluted with chloroform (50 ml) and the solution was washed with water (100 ml), dried over magnesium sulphate and evaporated to give a colourless oil, which solidified on trituration with water. The solid material was dried and recrystallised from a mixture of toluene (15 ml) and hexane (15 ml) to give 1-(3,4-dichlorobenzyl)imidazole-N,N'-dimethyl-4,5-dicarboxamide, m.p. 128°–129° C., (2.0 g) as colourless crystals.

EXAMPLE 4

By proceeding in a similar manner to that hereinbefore described in Example 1 but replacing the 1-(3,4-dichlorobenzyl)imidazole-4,5-dicarboxylic acid by the appropriate substituted imidazole-4,5-dicarboxylic acids, there were prepared:

1-(4-bromo-3-chlorobenzyl)imidazole-N,N'-dimethyl-4,5-dicarboxamide, m.p. 127°–128° C. (after crystallisation from ethanol), from 1-(4-bromo-3-chlorobenzyl)imidazole-4,5-dicarboxylic acid;

1-(3-bromo-4-methylbenzyl)imidazole-N,N'-dimethyl-4,5-dicarboxamide, m.p. 121.5°–122° C. (after crystallisation from ethanol), from 1-(3-bromo-4-methylbenzyl)imidazole-4,5-dicarboxylic acid;

1-(3-chloro-4-methylbenzyl)imidazole-N,N'-dimethyl-4,5-dicarboxamide, m.p. 110.5°–111° C. [after crystallisation from a mixture of toluene and (light petroleum b.p. 60°–80° C.)], from 1-(3-chloro-4-methylbenzyl)-imidazole-4,5-dicarboxylic acid;

1-(4-chloro-3-methylbenzyl)imidazole-N,N'-dimethyl-4,5-dicarboxamide, m.p. 149°–151° C. (after crystallisation from ethanol), from 1-(4-chloro-3-methylbenzyl)imidazole-4,5-dicarboxylic acid;

(±)-1-[1-(3-chlorophenyl)ethyl]imidazole-N,N'-dimethyl-4,5-dicarboxamide, m.p. 86°–88° C. (after crystallisation from ethanol), from (±)-1-[1-(3-chlorophenyl)ethyl]imidazole-4,5-dicarboxylic acid;

(±)-1-[1-(4-chlorophenyl)ethyl]imidazole-N,N'-dimethyl-4,5-dicarboxamide, m.p. 129°–130° C. (after crystallisation from ethanol), from (±)-1-[1-(4-chlorophenyl)-ethyl]imidazole-4,5-dicarboxylic acid;

(±)-1-[1-(3,4-dibromophenyl)ethyl]imidazole-N,N'-dimethyl-4,5-dicarboxamide, m.p. 118°–120° C. (after crystallization from cyclohexane), from (±)-1-[1-(3,4-dibromophenyl)ethyl]imidazole-4,5-dicarboxylic acid;

(±)-1-[1-(3-trifluoromethylphenyl)ethyl]imidazole-N,N'-dimethyl-4,5-dicarboxamide, b.p. 197°–199° C./0.3 mmHg, from (±)-1-[1-(3-trifluoromethylphenyl)ethyl]imidazole-4,5-dicarboxylic acid;

(±)-1-[1-(4-trifluoromethylphenyl)ethyl]imidazole-N,N'-dimethyl-4,5-dicarboxamide, m.p. 95°–97° C. (after crystallisation from cyclohexane), from (±)-1-[1-(4-trifluoromethylphenyl)ethyl]imidazole-4,5-dicarboxylic acid;

(±)-1-[1-(3,4-dichlorophenyl)propyl]imidazole-N,N'-dimethyl-4,5-dicarboxamide, m.p. 91°–93° C. (after crystallisation from cyclohexane), from (±)-1-[1-(3,4-dichlorophenyl)propyl]imidazole-4,5-dicarboxylic acid; and (±)-1-[1-(3,4-dichlorophenyl)butyl]imidazole-N,N'-dimethyl-4,5-dicarboxamide, m.p. 134°–135° C. (after crystallisation from toluene), from (±)-1-[1-(3,4-dichlorophenyl)butyl]imidazole-4,5-dicarboxylic acid.

The benzylimidazole-4,5-dicarboxylic acids used as starting materials in the above preparations were prepared in a similar manner to that hereinbefore described in Example 1 for the preparation of 1-(3,4-dichlorobenzyl)-imidazole-4,5-dicarboxylic acid but replacing the 1-(3,4-dichlorobenzyl) -4,5-dicyanoimidazole by the appropriate benzyldicyanoimidazoles:

1-(4-bromo-3-chlorobenzyl)imidazole-4,5-dicarboxylic acid, m.p. 262° C. with decomposition, from 1-(4-bromo-3-chlorobenzyl)-4,5-dicyanoimidazole;

1-(3-bromo-4-methylbenzyl)imidazole-4,5-dicarboxylic acid, m.p. 259° C. with decomposition, from 1-(3-bromo-4-methylbenzyl)-4,5-dicyanoimidazole;

1-(3-chloro-4-methylbenzyl)imidazole-4,5-dicarboxylic acid, m.p. 251°–253° C. with decomposition, from 1-(3-chloro-4-methylbenzyl)-4,5-dicyanoimidazole;

1-(4-chloro-3-methylbenzyl)imidazole-4,5-dicarboxylic acid, m.p. 266° C. with decomposition, from 1-(4-chloro-3-methylbenzyl)-4,5-dicyanoimidazole;

(±)-1-[1-(3-chlorophenyl)ethyl]imidazole-4,5-dicarboxylic acid, m.p. 173° C. with decomposition, from (±)-1-[1-(3-chlorophenyl)ethyl]-4,5-dicyanoimidazole;

(±)-1-[1-(4-chlorophenyl)ethyl]imidazole-4,5-dicarboxylic acid, m.p. 185° C. with decomposition, from (±)-1-[1-(4-chlorophenyl)ethyl]-4,5-dicyanoimidazole;

(±)-1-[1-(3,4-dibromophenyl)ethyl]imidazole-4,5-dicarboxylic acid, m.p. 179°–189° C. with decomposition, from (±)-1-[1-(3,4-dibromophenyl)ethyl]-4,5-dicyanoimidazole;

(±)-1-[1-(3-trifluoromethylphenyl)ethyl]imidazole-4,5-dicarboxylic acid, m.p. 183° C. with decomposition, from (±)-1-[1-(3-trifluoromethylphenyl)ethyl]-4,5-dicyanoimidazole;

(±)-1-[1-(4-trifluoromethylphenyl)ethyl]-imidazole-4,5-dicarboxylic acid, m.p. 195° C. with decomposition, from (±)-1-[1-(4-trifluoromethylphenyl)-ethyl]-4,5-dicyanoimidazole;

(±)-1-[1-(3,4-dichlorophenyl)propyl]imidazole-4,5-dicarboxylic acid, m.p. 185° C. with decomposition, from (±)-1-[1-(3,4-dichlorophenyl)propyl]-4,5-dicyanoimidazole; and (±)-1-[1-(3,4-dichlorophenyl)butyl]imidazole-4,5-dicarboxylic acid m.p. 173°–174° C. with decomposition from (±)-1-[1-(3,4-dichlorophenyl)butyl]-4,5-dicyanoimidazole.

The benzyldicyanoimidazoles used as starting materials in the above preparations were prepared in a similar manner to that hereinbefore described in Example 1 for the preparation of 1-(3,4-dichlorobenzyl)-4,5-dicyanoimidazole but replacing the 3,4-dichlorobenzyl chloride by the appropriate substituted benzyl halide:

1-(4-bromo-3-chlorobenzyl)-4,5-dicyanoimidazole, m.p. 138°–139° C. (after crystallisation from ethanol), from 4-bromo-3-chlorobenzyl bromide;

1-(3-bromo-4-methylbenzyl)-4,5-dicyanoimidazole, m.p. 113°–114.5° C. (after crystallisation from aqueous ethanol), from 3-bromo-4-methylbenzyl chloride;

1-(3-chloro-4-methylbenzyl)-4,5-dicyanoimidazole, m.p. 120°–121° C. (after crystallisation from aqueous ethanol), from 3-chloro-4-methylbenzyl chloride [described by Stephen et al., J. Chem. Soc. 117, 524 (1920)];

1-(4-chloro-3-methylbenzyl)-4,5-dicyanoimidazole, m.p. 82.5°–83.5° C. (after crystallisation from aqueous ethanol), from 4-chloro-3-methylbenzyl chloride [described by Horvath, U.S. Pat. No. 2,965,682 (1960)];

(±)-1-[1-(3-chlorophenyl)ethyl]-4,5-dicyanoimidazole, m.p. 74°–77° C., from (±)-1-(3-chlorophenyl)-ethyl chloride [described by Usui et al., Japanese Kokai 73-67, 228 (1973)];

(±)-1-[1-(4-chlorophenyl)ethyl]-4,5-dicyanoimidazole, m.p. 92°–93° C., from (±)-1-(4-chlorophenyl)-ethyl chloride [described by Protwa et al., Collection Czech. Chem. Commun. 27, 2102 (1962)];

(±)-1-[1-(3,4-dibromophenyl)ethyl]-4,5-dicyanoimidazole, m.p. 175°–177° C. (after crystallisation from toluene), from (±)-1-(3,4-dibromophenyl)ethyl chloride;

(±)-1-[1-(3-trifluoromethylphenyl)ethyl]-4,5-dicyanoimidazole, b.p. 188°–190° C./0.15 mmHg, from (±)-1-(3-trifluoromethylphenyl)ethyl bromide;

(±)-1-[1-(4-trifluoromethylphenyl)ethyl]-4,5-dicyanoimidazole, b.p. 182°–184° C./0.1 mmHg, from (±)-1-(4-trifluoromethylphenyl)ethyl bromide;

(±)-1-[1-(3,4-dichlorophenyl)propyl]-4,5-dicyanoimidazole, m.p. 95°–97° C. [after crystallisation from light petroleum (b.p. 100°–120° C.)], from (±)-1-(3,4-dichlorophenyl)propyl chloride; and (±)-1-[1-(3,4-dichlorophenyl)butyl]-4,5-dicyanoimidazole as a brown oil, from (±)-1-(3,4-dichlorophenyl)butyl chloride.

The benzyl halides used as starting materials in the above preparations were prepared (a) in a similar manner to that hereinbefore described in Example 1 for the preparation of 3,4-dibromobenzyl chloride but replacing the 3,4-dibromobenzyl alcohol by the appropriate benzyl alcohol:

3-bromo-4-methylbenzyl chloride, as a clear mobile oil, from 3-bromo-4-methylbenzyl alcohol;

(±)-1-(3,4-dibromophenyl)ethyl chloride, b.p. 90°–100° C./0.25 mmHg, from (±)-1-(3,4-dibromophenyl)ethanol [described by Koton et al., Zhur. Priklad, Khim. 26, 666 (1953)];

(±)-1-(3,4-dichlorophenyl)propyl chloride, b.p. 82°–85° C./0.25 mmHg, from (±)-1-(3,4-dichlorophenyl)propanol [described by Shell Oil Co., U.S. Pat. No. 3,840,579 (1974)], and (±)-1-(3,4-dichlorophenyl)butyl chloride, as a light brown oil, from (±)-1-(3,4-dichlorophenyl)butanol; and (b) bromine (32.5 g≡10.4 ml) was added over 15 minutes to a stirred mixture of (±)-1-(3-trifluoromethylphenyl)-ethanol [38 g, described by Overberger et al., Org. Synth. Coll. 3, 200 (1955)], triphenylphosphine (56 g) and dry dimethylformamide (200 ml) in an atmosphere of nitrogen. The temperature of the mixture was maintained at 40°–50° C. by ice-cooling. Further bromine was added dropwise to give a permanent orange colour and after stirring for 15 minutes the mixture was poured into a mixture of ice-water (1 liter) and hexane (500 ml). The mixture was filtered and the solid material was washed well with hexane. The hexane solutions were combined, washed with water (4×100 ml), dried over sodium sulphate and distilled to give (±)-1-(3-trifluoromethylphenyl)ethyl bromide, b.p. 98°–105° C./15 mmHg, as a clear mobile oil.

By proceeding in a similar manner but replacing the (±)-1-(3-trifluoromethylphenyl)ethanol with the appropriate benzyl alcohol there were prepared:

(±)-1-(4-trifluoromethylphenyl)ethyl bromide b.p. 81°–84° C./13 mmHg, from (±)-1-(4-trifluoromethylphenyl)-ethanol (described by Novotny et al., J. Pharm. Sci., 1973, 62, 910); and (c) 4-bromo-3-chlorotoluene [31.8 g, described by Cohen and Raper, J. Chem. Soc., 85, 1267 (1904)] was heated with N-bromosuccinimide (27.5 g) and benzoyl peroxide (3.6 g) in carbon tetrachloride (75 ml) at reflux for 10 hours. The cooled solution was filtered, washed with aqueous ferrous sulphate solution, dried over magnesium sulphate, filtered and evaporated to dryness. 4-Bromo-3-chlorobenzyl bromide (44 g) was obtained as a pale orange oil.

The benzyl alcohols used as starting materials in (a) and (b) above were prepared (i) in a similar manner to that hereinbefore described in Example 1 for the preparation of 3,4-dibromobenzyl alcohol but replacing the 3,4-dibromobenzoic acid by 3-bromo-4-methylbenzoic acid [described by Jannasch and Dieckmann, Ann., 171, 83 (1874)]; there was obtained 3-bromo-4-methylbenzyl alcohol as a clear orange oil of sufficient purity for subsequent reaction; and (ii) sodium borohydride (14.9 g) was added in portions over 30 minutes to a stirred solution of 3,4-dichlorobutyrophenone [65.3 g, described by Foerster et al., East German Patent No. 45,721 (1966)] at 0°–10° C. The mixture was heated at reflux for 2 hours and cooled; sodium hydroxide solution (300 ml, 2N) was added and the mixture was heated at reflux for 30 minutes. Methanol was removed by evaporation and the aqueous solution was extracted with diethyl ether (5×200 ml). The combined extracts were washed with water (200 ml), hydrochloric acid (200 ml, 2N), and water (5×200 ml); dried over magnesium sulphate and evaporated to dryness. (±)-1-(3,4-Dichlorophenyl)butanol (65 g) was obtained as a light brown oil of sufficient purity for subsequent reaction.

EXAMPLE 5

By proceeding in a similar manner to that hereinbefore described in Example 3 but replacing the 3,4-dichlorobenzyl chloride by the appropriate benzyl halide there were prepared:

1-(3,4-diiodobenzyl)imidazole-N,N'-dimethyl-4,5-dicarboxamide, m.p. 155°–156° C. (after crystallisation from ethanol), from 3,4-diiodobenzyl bromide;

1-(3,4,5-trichlorobenzyl)imidazole-N,N'-dimethyl-4,5-dicarboxamide, m.p. 128°–130° C. (after crystallisation from ethanol), from 3,4,5-trichlorobenzyl chloride; [prepared as described by Chiavarelli, Gazz. chim. Ital. 85, 1405 (1955)];

1-[3,5-bis(trifluoromethyl)benzyl]imidazole-N,N'-dimethyl-4,5-dicarboxamide, m.p. 142°–144° C. (after crystallisation from cyclohexane) from 3,5-bis(trifluoromethyl)benzyl bromide (described by Ambrus, U.S. Pat. No. 3,625,970).

(±)-1-[1-(4-iodophenyl)ethyl]imidazole-N,N'-dimethyl-4,5-dicarboxamide, m.p. 132°–134° C. (after crystallisation from aqueous ethanol), from (±)-1-(4-iodophenyl)ethyl bromide;

(±)-1-[1-(4-trifluoromethoxyphenyl)ethyl]imidazole-N,N'-dimethyl-4,5-dicarboxamide, m.p. 78°–79° C. [after crystallisation from light petroleum (b.p. 60°–0° C.)], from (±)-1-(4-trifluoromethoxyphenyl)ethyl bromide;

(±)-1-{1-[3,5-bis(trifluoromethyl)phenyl]ethyl}-imidazole-N,N'-dimethyl-4,5-dicarboxamide, m.p. 132°–134° C. (after crystallisation from cyclohexane) from 1-[3,5-bis(trifluoromethyl)phenyl]ethyl bromide;

(±)-1-[1-(3,4-dichlorophenyl)pentyl]imidazole-N,N'-dimethyl-4,5-dicarboxamide, m.p. 142°–143° C. [after crystallisation from light petroleum (b.p. 60°–80° C.)]from (±)-1-(3,4-dichlorophenyl)pentyl bromide;

(±)-1-[1-(3,4-dichlorophenyl)hexyl]imidazole-N,N'-dimethyl-4,5-dicarboxamide, m.p. 114°–115° C. [after crystallisation from light petroleum (b.p. 60°–80° C.)], from (±)-1-(3,4-dichlorophenyl)hexyl bromide;

(±)-1-[1-(3,4-dichlorophenyl)heptyl]imidazole-N,N'-dimethyl-4,5-dicarboxamide, m.p. 97.5°–99° C. [after crystallisation from light petroleum (b.p. 60°–80° C.)], from (±)-1-(3,4-dichlorophenyl)heptyl chloride; and (±)-1-[1-(3,4-dichlorophenyl)nonyl]imidazole-N,N'-dimethyl-4,5-dicarboxamide, m.p. 79°–79.5° C. [after crystallisation from light petroleum (b.p. 60°–80° C.)], from (±)-1-(3,4-dichlorophenyl)nonyl chloride.

The benzyl halides used as starting materials in the above preparations were prepared:

(a) in a similar manner to that hereinbefore described in Example 1 for the preparation of 3,4-dibromobenzyl chloride but replacing the 3,4-dibromobenzyl alcohol by (±)-1-(3,4-dichlorophenyl)heptanol:

(±)-1-(3,4-dichlorophenyl)heptyl chloride as a colourless oil;

(b) by proceeding in a similar manner to that hereinbefore described in Example 4(b) for the preparation of (±)-1-(3-trifluoromethylphenyl)ethyl bromide but replacing the (±)-1-(3-trifluoromethylphenyl)ethanol by the appropriate alcohol:

(+)-1-(4-iodophenyl)ethyl bromide, as an orange oil, from (+)-1-(4-iodophenyl)ethanol;

(+)-1-(4-trifluoromethoxyphenyl)ethyl bromide, as an orange oil, from (+)-1-(4-trifluoromethoxyphenyl)ethanol;

(+)-1-[3,5-bis(trifluoromethyl)phenyl]ethyl bromide, b.p. 97°–98° C./10 mmHg, from (+)-1-[3,5-bis(trifluoromethyl)phenyl]ethanol [described by McBee and Sanford, JACS 72, 4054 (1950)];

(+)-1-(3,4-dichlorophenyl)pentyl bromide, as a light orange oil, from (+)-1-(3,4-dichlorophenyl)pentanol;

(+)-1-(3,4-dichlorophenyl)hexyl bromide, as a yellow oil, from (+)-1-(3,4-dichlorophenyl)hexanol; and (+)-1-(3,4-dichlorophenyl)nonyl bromide, as a yellow oil, from (+)-1-(3,4-dichlorophenyl)nonanol; and (c) by proceeding in a similar manner to that hereinbefore described in Example 4(c) for the preparation of 4-bromo-3-chlorobenzyl bromide but replacing the 4-bromo-3-chlorotoluene by 3,4-diiodotoluene [(described by Willgerodt and Simonis, Ber. 39, 279 (1906)]:

3,4-diiodobenzyl bromide, m.p. 85°–87° C.

Some of the benzyl alcohols used as starting materials in the above preparations were made in a similar manner to that hereinbefore described in Example 4(ii) for the preparation of (+)-1-(3,4-dichlorophenyl)butanol but replacing the 3,4-dichlorobutyrophenone by the appropriate alkanophenone:

(+)-1-(4-iodophenyl)ethanol, as an orange oil, from 4-iodoacetophenone [described by Campaigne et al., J. Org. Chem., 24, 1229 (1959)];

(+)-1-(3,4-dichlorophenyl)pentanol, from 3',4'-dichlorovalerophenone;

(+)-1-(3,4-dichlorophenyl)hexanol, as a pale yellow oil, from 3',4'-dichlorohexanophenone;

(+)-1-(3,4-dichlorophenyl)heptanol, as a near colourless oil, from 3',4'-dichloroheptanophenone; and (+)-1-(3,4-dichlorophenyl)nonanol, as a near colourless oil, from 3',4'-dichlorononanophenone.

(+)-1-(4-Trifluoromethoxyphenyl)ethanol was prepared as follows:

Methyl magnesium iodide [prepared from magnesium (3.5 g) and methyl iodide (20.5 g)] in diethyl ether (50 ml) was treated with a solution of 4-trifluoromethoxybenzaldehyde [20 g, described by Yagupolskii and Troitskaya, Zhur. Obschii Khim., 30, 3129 (1960)] in diethyl ether (25 ml) at reflux with stirring. After the addition the mixture was heated at reflux for 6 hours. The cooled solution was treated with a solution of ammonium chloride (35 g) in water (100 ml) at 0°–5° C. The organic layer was separated and the aqueous layer was washed with diethyl ether (3×50 ml). The ether solution and washings were combined, washed with water (2×100 ml), dried over sodium sulphate and evaporated to dryness. (+)-1-(4-Trifluoromethoxyphenyl)ethanol (20.3 g) was obtained as a clear colourless oil of sufficient purity for subsequent reaction.

3,4-Dichlorovalerophenone used in one of the above preparations was made as follows:

Valeryl chloride (60.3 g) was added to a well stirred solution of aluminium chloride (70 g) in o-dichlorobenzene (73.5 g). The temperature rose from 25° to 47° C. The solution was cautiously heated on a steam bath for 3 hours, cooled and poured into a mixture of ice (500 g) and concentrated hydrochloric acid (100 ml). The layers were separated and the aqueous phase was extracted with diethyl ether (3×250 ml).

The organic phase and the ethereal extracts were combined, washed with water (2×250 ml), saturated aqueous sodium carbonate solution (4×100 ml) and water (3×250 ml), dried over sodium sulphate, and evaporated to dryness. The solid residue was crystallised from light petroleum (b.p. 60°–80° C.; 150 ml) to give 3',4'-dichlorovalerophenone (41 g), m.p. 40°–41° C., as light brown crystals.

By proceeding in a similar manner but replacing valeryl chloride by the appropriate alkanoyl chloride there were prepared:

3',4'-dichlorohexanophenone, b.p. 115°–150° C./0.2 mmHg, m.p. <35° C., from hexanoyl chloride;

3',4'-dichloroheptanophenone, b.p. 140°–200° C./0.3 mmHg, from heptanoyl chloride; and 3',4'-dichlorononanophenone, b.p. 155°–157° C./0.25 mmHg, from nonanoyl chloride.

REFERENCE EXAMPLE 1

Benzyldicyanoimidazoles useful as starting materials in the preparation of final stage intermediates of Process 1 described above were also prepared as follows:

2-Amino-3-(3,4-dichlorobenzylamino)maleonitrile (10.7 g) was heated on a steam bath in a mixture of ethanol (4 ml) and triethylorthoformate (12 g) containing concentrated sulphuric acid (0.02 ml) for 1 hour. The solution was evaporated to dryness to give a semisolid, which was crystallised from ethanol (50 ml) to give 1-(3,4-dichlorobenzyl)-4,5-dicyanoimidazole (3.0 g), m.p. 131°–132.5° C., as pale yellow crystals.

By proceeding in a similar manner but replacing the 2-amino-3-(3,4-dichlorobenzylamino)maleonitrile by (+)-2-amino-3-[1-(4-chlorophenyl)ethylamino]maleonitrile there was prepared (+)-1-[1-(4-chlorophenyl)ethyl]-4,5-dicyanoimidazole, m.p. 95°–96° C. [after crystallisation from a mixture of diethyl ether (100 ml) and hexane (100 ml)].

The 2-amino-3-benzylamino-maleonitriles used in the above preparations were prepared as follows:

2-Amino-3-(3,4-dichlorobenzylidineamino)maleonitrile (53 g) was dissolved in a mixture of methanol (300 ml) and tetrahydrofuran (500 ml) and the solution was treated with portions of sodium borohydride (7.6 g) over 1 hour at room temperature. The solution was allowed to stand for 1 hour and was poured into water (3 liters). The brown solid which separated was filtered off and crystallised from a mixture of toluene (600 ml) and ethanol (50 ml) to give 2-amino-3-(3,4-dichlorobenzylamino)maleonitrile (28.5 g), m.p. 158°–160° C., as fawn crystals.

By proceeding in a similar manner but replacing the 2-amino-3-(3,4-dichlorobenzylidineamino)maleonitrile by 2-amino-2-[1-(4-chlorophenyl)ethylidineamino]-maleonitrile there was obtained (+)-2-amino-3-[1-(4-chlorophenyl)ethylamino]maleonitrile, m.p. 145°–146° C. (after crystallisation from toluene).

The azomethines needed as starting materials in the previous preparations were made as follows:

A solution of diaminomaleonitrile (27 g) in tetrahydrofuran (250 ml) containing concentrated sulphuric acid (10 drops) was treated with 3,4-dichlorobenzaldehyde. The mixture was allowed to stand overnight and was diluted with light petroleum (b.p. 60°–80° C.; 250 ml) and cooled to 0° C. Yellow crystals of 2-amino-3-(3,4-dichlorobenzylidineamino)maleonitrile (53 g), m.p. 237°–240° C., were obtained by filtration.

By proceeding in a similar manner but replacing the 3,4-dichlorobenzaldehyde by 4-chloroacetophenone there was obtained 2-amino-3-[1-(4-chlorophenyl)ethylideneamino]maleonitrile, m.p. 154°–156° C. (after crystallisation from diethyl ether (200 ml).

According to a further feature of the present invention, there are provided compositions suitable for herbicidal use comprising one or more of the imidazole derivatives of general formula I in association with, and preferably homogeneously dispersed in, one or more compatible herbicidally-acceptable diluents or carriers (i.e. diluents or carriers of the type generally accepted in the art as being suitable for use in herbicidal compositions and which are compatible with compounds of general formula I). The term "homogeneously dispersed" is used to include compositions in which the compounds of general formula I are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula I.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula I with solid diluents or by impregnating the solid diluents or carriers with solutions of the compounds of general formula I in volatile solvents, evaporating the solvents and, if necessary, grinding the products so as to obtain powders. Granular formulations may be prepared by absorbing the compounds of general formula I (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers. Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compound of general formula I may be used in the form of self-emulsifying concentrates containing the active substances dissolved in the emulsifying agents or in solvents containing emulsifying agents compatible with the active substances, the simple addition of water to such concentrates producing compositions ready for use.

Herbicidal compositions according to the present invention may also contain, if desired, conventional adjuvants such as adhesives, colouring agents and corrosion inhibitors. These adjuvants may also serve as carriers or diluents.

Herbicidal compositions according to the present invention may also comprise the compounds of general formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example alachlor [α-chloro-2,6-diethyl-N-(methoxymethyl)acetanilide], asulam [methyl(4-aminobenzenesulphonyl)carbamate], atrazine [2-chloro-4-ethylamino-6-isopropylamino-1,3,5-triazine], barban [4-chlorobut-2-ynyl N-(3-chlorophenyl)carbamate], benzoylprop-ethyl [ethyl N-benzoyl-N-(3,4-dichlorophenyl-2-aminopropionate], bromoxynil 3,5-dibromo-4-hydroxybenzonitrile], butachlor [N-(butoxymethyl)-α-chloro-2,6-diethylacetanilide], butylate [S-ethyl N,N-diisobutyl(thiocarbamate)], carbetamide [D-N-ethyl-2-(phenylcarbamoyloxy)propionamide], chlorfenprop-methyl [methyl 2-chloro-3-(4-chlorophenyl) propionate], chlorpropham [isopropyl N-(3-chlorophenyl)carbamate], chlorotoluron [N'-(3-chloro-4-methylphenyl)-N,N-dimethylurea], cyanazine [2-chloro-4-(1-cyano-1-methylethylamino)-6-ethylamino-1,3,5-triazine], cycloate [N'-cyclohexyl-N-ethyl-S-ethyl(thiocarbamate)], 2,4-D[2,4-dichlorophenoxyacetic acid], dalapon [2,2-dichloropropionic acid], 2,4-DB [4-(2,4-dichlorophenoxy)butyric acid], desmedipham [3-(ethoxycarbonylamino)phenyl N-phenyl-carbamate], diallate [S-2,3-dichloroallyl-N,N-di-isopropyl(thiocarbamate)], dicamba [3,6-dichloro-2-methoxybenzoic acid], dichlorprop [(+)-2-(2,4-dichlorophenoxy)propionic acid], difenzoquat [1,2-dimethyl-3,5-diphenyl-pyrazolium salts], dimefuron {4-[2-chloro-4-(3,3-dimethylureido)phenyl]-2-t-butyl-1,3,4-oxadiazolin-5-one}, dinitramine [N$^1$,N$^1$-diethyl-2,6-dinitro-4-trifluoromethyl-m-phenylenediamine], diuron [N'-(3,4-dichlorophenyl)-N,N-dimethylurea], EPTC [S-ethyl N,N-dipropyl(thiocarbamate)], ethofumesate [2-ethoxy-2,3-dihydro-3,3-dimethylbenzofuran-5-yl methylsulphonate, flampropisopropyl [isopropyl (+)-2-(N-benzoyl-3-chloro-4-fluoroanilino)propionate], flamprop-methyl [methyl (+)-2-(N-benzoyl-3-chloro-4-fluoroanilino)propionate], fluometuron [N'-(3-trifluoromethylphenyl)-N,N-dimethylurea], ioxynil [4-hydroxy-3,5-di-iodobenzonitrile], isoproturon [N'-(4-isopropylphenyl)-N,N-dimethylurea], linuron [N-(3,4-dichlorophenyl)-N-methoxy-N-methylurea], MCPA [4-chloro-2-methylphenoxyacetic acid], MCPB [4-(4-chloro-2-methylphenoxy)butyric acid], mecoprop [(+)-2-(4-chloro-2-methylphenoxy)propionic acid], metamitron [4-amino-3-methyl-6-phenyl-1,2,4-triazin-5(4H)-one], methabenzthiazuron [N-(benzothiazol-2-yl)-N,N'-dimethylurea], metribuzin [4-amino-6-t-butyl-3-(methylthio)-1,2,4-triazin-5(4H)-one, molinate [S-ethyl N,N-hexamethylene(thiocarbamate)], oxadiazon [3-(2,4-dichloro-5-isopropoxyphenyl)-5-t-butyl-1,3,4-oxadiazolin-2-one], paraquat [1,1'-dimethyl-4,4'-bipyridylium salts], pebulate [S-propyl N-butyl-N-ethyl(thiocarbamate)], phenmedipham [3-(methoxycarbonylamino)-phenyl N-(3-methylphenyl)carbamate], prometryne [4,6-bisisopropylamino-2-methylthio-1,3,5-triazine], propachlor [α-chloro-N-isopropylacetanilide], propanil [N-(3,4-dichlorophenyl)propionamide], propham [isopropyl N-phenylcarbamate], pyrazone [5-amino-4-chloro-2-phenylpyridazin-3(2H)-one], simazine [2-chloro-4,6-bisethylamino-1,3,5-triazine], TCA (trichloroacetic acid), thiobencarb [S-(4-chlorobenzyl)-N,N-diethylthiolcarbamate], tri-allate [S-2,3,3-trichloroallyl N,N-di-isopropyl(thiocarbamate)] and trifluralin [2,6-dinitro-N,N-dipropyl-4-trifluoromethylaniline]; insecticides, e.g. naphth-1-yl N-methylcarbamate; and fungicides, e.g. 2,6-dimethyl-4-tridecyl-morpholine, methyl N-(1-butylcarbamoyl-benzimidazol-2-yl)-carbamate and 1,2-bis(3-methoxycarbonyl-2-thioureido) benzene. Other biologically active materials which may be included in, or used in conjunction with, the herbicidal compositions of the present invention are plant growth regulators, e.g. maleic hydrazide, N-dimethylaminosuccinamic acid, (2-chloroethyl)trimethylammonium chloride and 2-chloroethane phosphonic acid; or fertilizers, e.g. containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilised in the form of conventional derivatives, for example alkali metal and amine salts and esters.

According to a further feature of the present invention there is provided an article of manufacture comprising at least one of the imidazole derivatives of general formula I or, as is preferred, a herbicidal composition as hereinbefore described, and preferably a herbicidal concentrate which must be diluted before use, comprising at least one of the imidazole derivatives of general formula I within a container for the aforesaid derivative or derivatives of general formula I, or a said herbicidal composition, and instructions physically associated with the aforesaid container setting out the manner in which the aforesaid derivative or derivatives of general formula I or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the imidazole derivatives or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.25 kg and 20 kg of active material per hectare in the manner and for the purposes hereinbefore described.

The following Examples illustrate herbicidal compositions according to the present invention.

EXAMPLE 6

An aqueous suspension concentrate is formed from:
1-(3,4-dichlorobenzyl)imidazole-N,N'-dimethyl-4,5-dicarboxamide: 30% w/v
Agrilan A (an anionic/nonionic emulsifier): 5% w/v
distilled water: 100% by volume by intimately mixing the ingredients and grinding in a ball-mill for 24 hours. The concentrate thus obtained may be dispersed in water and applied at a rate of 2.0 kg of imidazole derivative in 200 liters of spray fluid per hectare to a crop-growing area planted with maize to control the growth of *Abutilon theophrasti, Ipomea purpurea, Chenopodium album, Amaranthus retroflexus, Datura stramonium, Xanthium strumarium* and *Polygonum convolvulus* by post-emergence application to the foliage of the weeds after the emergence of both the weeds and the crop.

The 1-(3,4-dichlorobenzyl)imidazole-N,N'-dimethyl-4,5-dicarboxamide may, if desired, be replaced in the above aqueous suspension concentrate by any other compound of general formula I, for example 1-(3,4-dibromobenzyl)imidazole-N,N'-dimethyl-4,5-dicarboxamide or 1-(4-trifluoromethylbenzyl)imidazole-N,N'-dimethyl-4,5-dicarboxamide.

EXAMPLE 7

A wettable powder concentrate is formed from:
1-(3,4-dichlorobenzyl)imidazole-N,N'-dimethyl-4,5-dicarboxamide: 50% w/w
Ethylan BCP (a nonylphenyl/ethylene oxide condensate containing 9 moles of ethylene oxide per mol of phenol): 2.5% w/w
Clarcelflo SAS 132 (synthetic magnesium silicate carrier): 47.5% w/w by dissolving the imidazole and Ethylan BCP in the minimum volume of acetone and adding the solution to the Clarcelflo in a blender. After the acetone has evaporated, the product is ground in a hammer-mill to give a wettable powder which may be diluted with water and applied at a rate of 4.0 kg of imidazole derivative in 400 liters of spray fluid per hectare to a crop-growing area sown with soyabean to control the growth of *Amaranthus retroflexus, Chenopodium album, Setaria viridis, Echinochloa crus-galli* and *Digitaria sanguinalis* by pre-emergence application to the surface of the soil after sowing of the crop but before emergence of the weeds.

The 1-(3,4-dichlorobenzyl)imidazole-N,N'-dimethyl-4,5-dicarboxamide may, if desired, be replaced in the above wettable powder concentrate by any other compound of general formula I, for example 1-[1-(3,4-dichlorophenyl)ethyl]imidazole-N,N'-dimethyl-4,5-dicarboxamide, 1-(4-trifluoromethylbenzyl)imidazole-N,N'-dimethyl-4,5-dicarboxamide or 1-[1-(4-trifluoromethylphenyl)ethyl]imidazole-N,N'-dimethyl-4,5-dicarboxamide.

EXAMPLE 8

An emulsifiable concentrate is formed from:
1-(3,4-dichlorobenzyl)imidazole-N,N'-dimethyl-4,5-dicarboxamide 10% w/v
Atlox 4855 (a polyoxyethylene triglyceride/alkyl aryl sulphonate emulsifier blend): 4% w/v
Tween 20 [polyoxyethylene (20) sorbitan monolaurate emulsifier]: 1% w/v
methyl phenyl ether: to 100% by volume by dissolving the imidazole derivative, Atlox 4855 and Tween 20 in a portion of the methyl phenyl ether, if necessary with heating, and then adding, with stirring, the remainder of the methyl phenyl ether. The emulsifiable concentrate thus obtained may be diluted with water and applied at a rate of 1.0 kg of imidazole derivative in 100 liters of spray fluid per hectare to a crop-growing area planted with wheat to control the growth of *Stellaria media, Sinapis arvensis, Chenopodium album, Spergula arvensis, Urtica ureus, Amsinkia intermedia, Polygonum convolvulus, Galeopsis Tetrahit* and *Lamium purpureum* by post-emergence application to the foliage of these weeds after the emergence of both crop and weeds.

The 1-(3,4-dichlorobenzyl)imidazole-N,N'-dimethyl-4,5-dicarboxamide may, if desired, be replaced in the above emulsifiable concentrate by any other compound of general formula I, for example 1-(3,4-dibromobenzyl)-imidazole-N,N'-dimethyl-4,5-dicarboxamide or 1-(4-trifluoromethylbenzyl)imidazole-N,N'-dimethyl-4,5-dicarboxamide.

EXAMPLE 9

An emulsifiable suspension concentrate is formed from:
1-(3,4-dichlorobenzyl)imidazole-N,N'-dimethyl-4,5-dicarboxamide: 30% w/v
Atlox 4855: 5% w/v
Agrilan A: 5% w/v
HF Naphtha CW: to 100% by volume by intimately mixing the ingredients and grinding in a ball-mill for 24 hours.

The emulsifiable suspension concentrate thus obtained may be diluted with water and applied at a rate of 10 kg of imidazole derivative in 300 liters of spray fluid per hectare to a newly planted orchard to control the growth of broad leaf and grass weeds for a prolonged period by directed application around the base of the trees before or after weed emergence.

The 1-(3,4-dichlorobenzyl)imidazole-N,N'-dimethyl-4,5-dicarboxamide may, if desired, be replaced in the above emulsifiable suspension concentrate by any other compound of general formula I.

EXAMPLE 10

Granules are formed from:
1-(3,4-dichlorobenzyl)imidazole-N,N'-dimethyl-4,5-dicarboxamide: 5% w/w
Waxoline Red OS (4-ortho-tolylazoorthotoluidine-2-naphthol red dye): 0.2% w/w
30/60 Attaclay (sorptive silica clay) granules: to 100% by weight by dissolving the imidazole derivative and Waxoline Red OS in sufficient acetone to ensure complete impregnation of the granules and then spraying or dripping the acetone solution onto the granules and allowing the acetone to evaporate with constant stirring.

The granules thus formed may be spread evenly at a rate of 20 kg of granules (corresponding to 1.0 kg of imidazole derivative) per hectare over a flood-irrigated crop growing area planted with rice to control the growth of annual broad leaf weeds and aquatic weeds by application to the foliage of the weeds or to the water in which they are growing.

The 1-(3,4-dichlorobenzyl)imidazole-N,N'-dimethyl-4,5-dicarboxamide may, if desired, be replaced in the above granules by any other compound of general formula I.

EXAMPLE 11

A dust or powder is formed from:
1-(3,4-dichlorobenzyl)imidazole-N,N'-dimethyl-4,5-dicarboxamide: 2 to 10% w/w
finely-divided iron oxide: 1% w/w
talc superfine (synthetic magnesium silicate carrier): to 100% w/w by micronising the imidazole derivative and then intimately mixing the imidazole derivative, iron oxide and talc in a blender.

The finely divided dust or powder thus produced can be mixed with fertilized granules e.g. granules containing nitrogen, phosphorus, and potassium, and spread evenly by hand at a rate of 2.0 kg of imidazole derivative per hectare to a crop-growing area to control the growth of annual broad leaf weeds before emergence and prior to plating a crop of maize.

The 1-(3,4-dichlorobenzyl)imidazole-N,N'-dimethyl-4,5-dicarboxamide may, if desired, be replaced in the above dust or powder by any other compound of general formula I.

EXAMPLE 12

A water-dispersible concentrate is formed from:
1-(3,4-dichlorobenzyl)imidazole-N,N'-dimethyl-4,5-dicarboxamide: 10% w/v
Ethylan KED (a nonylphenol/ethylene oxide condensate containing 10 moles of ethylene oxide per mole of phenol): 20% w/v
dimethylformamide: to 100% by volume by dissolving the imidazole derivative and Ethylan KED in a portion of the dimethylformamide, if necessary with heating, and then adding, with stirring, the remainder of the dimethylformamide. The water-dispersible concentrate thus obtained may be diluted with water to give a suspension of finely-divided particles which may be applied at a rate of 1.5 kg of imidazole derivative in 150 liters of spray fluid per hectare to a crop growing area planted with onions to control the growth of annual broad leaf weeds, e.g. *Polygonum convulvulus, Chenopodium album* and *Sinapis arvensis,* by post-emergence application to the foliage of the weeds after the emergence of both weeds and crop.

The 1-(3,4-dichlorobenzyl)imidazole-N,N'-dimethyl-4,5-dicarboxamide may, if desired be replaced in the above water-dispersible concentrate by any other compound of general formula I.

EXAMPLE 13

An oil concentrate is formed from:
1-(3,4-dichlorobenzyl)imidazole-N,N'-dimethyl-4,5-dicarboxamide: 10% w/v
isophorone: to 100% by volume by dissolving the imidazole in the isophorone with stirring. The oil concentrate thus obtained may be applied, optionally after dilution with a suitable carrier oil (e.g. kerosene) to the edges of airfield runways and roads at a rate of 20 kg of imidazole derivative in 400 liters of spray fluid per hectare to control the growth and encroachment of annual and perennial broad leaf and grass weeds by directed application before or after emergence of the weeds.

The 1-(3,4-dichlorobenzyl)imidazole-N,N'-dimethyl-4,5-dicarboxamide may, if desired, be replaced in the above oil concentrate by any other compound of general formula I.

EXAMPLE 14

Foams may be obtained by the incorporation of 1% v/v of Perlankrol ESD-60 (sodium salt of synthetic primary alcohol ether sulphate) in the spray fluids obtained by the dilution with water of the concentrates described in Examples 6, 7, 8 and 12 and application of the spray fluid using suitable foam-producing nozzles.

The 1-(3,4-dichlorobenzyl)imidazole-N,N'-dimethyl-4,5-dicarboxamide may, if desired, be replaced in the above foams by any other compounds of general formula I.

These foams may be used to apply the compounds of general formula I as herbicides in situations in which it is necessary to reduce the risk of spray-drift. Thus, these foams may be used to control the growth of weeds in areas used to grow crops which are tolerant of the compounds of general formula I at the rate of application in question when the aforesaid areas are closely adjacent to areas used to grow crops which are more susceptible to the compounds of general formula I at that rate of application.

For example, a foam containing 1-(3,4-dichlorobenzyl)imidazole-N,N'-dimethyl-4,5-dicarboxamide may be applied accurately at a rate of 1.0 kg of imidazole derivative in 60 liters of spray fluid per hectare to an emerged row of maize plants to control annual broad leafed weeds by post-emergence application with negligible risk of spray-drift on to emerged tomato and brassica crop plants, which are more susceptible than maize to the imidazole derivatives, grown between the rows of maize.

EXAMPLE 15

An emulsifiable concentrate is formed from:
1-(3,4-dichlorobenzyl)imidazole-N,N'-dimethyl-4,5-dicarboxamide: 10% w/v
Duoterics MB1/MB2 (an anionic emulsifier blend containing calcium alkyl aryl sulphonate and alkyl phenol ethylene oxide condensates): 10% w/v
a 1:1 by volume mixture of cyclohexanone and Aromasol 'H' (an aromatic solvent consisting predominantly of isomeric trimethylbenzenes) to 100% by volume by dissolving the imidazole derivative and the Duoterics MB1/MB2 in a portion of the 1:1 cyclohexanone-Aromasol 'H' mixture, if necessary with heating, and adding, with stirring, the remainder of the cyclohexanone-Aromasol 'H' mixture. The emulsifiable concentrate thus obtained may be diluted with water and applied at a rate of 1.0 kg of imidazole derivative in 200 liters of spray fluid per hectare to a crop-growing area planted with sugar beet to control the growth of *Chenopodium album, Stellaria media, Polygonum convolvulus, Polygonum persicaria, Sinapis arvensis, Matricaria inodora* and *Solanum nigrum,* by post-emergence application to the foliage of these weeds after the emergence of both crop and weeds.

The 1-(3,4-dichlorobenzyl)imidazole-N,N'-dimethyl-4,5-dicarboxamide may, if desired, be replaced in the above emulsifiable concentrate by any other compound of general formula I, for example 1-(3,4-dibromobenzyl)-imidazole-N,N'-dimethyl-4,5-dicarboxamide or 1-(4-trifluoromethylbenzyl)imidazole-N,N'-dimethyl-4,5-dicarboxamide.

EXAMPLE 16

An aqueous suspension concentrate is formed from:
1-(4-trifluoromethylbenzyl)imidazole-N,N'-dimethyl-4,5-dicarboxamide: 40% w/v
Ethylan BCP (a nonylphenol-ethylene oxide condensation product containing 9 moles of ethylene oxide per mole of phenol): 5% w/v
silicone fluid (DC 200/1000Cs) (dimethylsilicone-1000Cs viscosity): 1% w/v
distilled water: to 100% by volume by intimately mixing the ingredients and grinding in a ballmill for 24 hours. The concentrate thus obtained may be dispersed in water and applied at a rate of 3.0 kg of imidazole derivative in 300 liters of spray fluid per hectare to a crop-growing area planted with sugar cane to control the growth of broad leaf weeds, for example *Amaranthus* spp., *Physalis* spp., *Portulaca oleracea* and *Ipomea* spp., and grass weeds, for example *Echinochloa crus-galli, Digitaria sanguinalis* and *Brachiaria plantaginea,* by pre- or post-emergence application before or after the emergence of the weeds and crop.

The 1-(4-trifluoromethylbenzyl)imidazole-N,N'-dimethyl-4,5-dicarboxamide may, if desired, be replaced in the above aqueous suspension concentrate by any other compound of general formula I, for example 1-[1-(4-trifluoromethylphenyl)ethyl]imidazole-N,N'-dimethyl-4,5-dicarboxamide.

We claim:

1. An imidazole derivative of the formula:

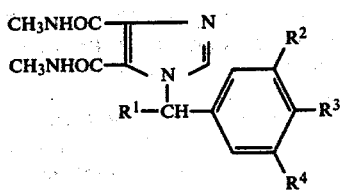

wherein R¹ represents hydrogen or a straight- or branched-chain alkyl group containing from 1 to 4 carbon atoms or a straight- or branched-chain alkenyl or alkynyl group containing from 2 to 4 carbon atoms, and one of R², R³ and R⁴, which may be the same or different, represents halogen, trifluoromethoxy, or a methyl, ethyl, propyl or isopropyl group substituted by one or more fluorine atoms, and the other symbols R², R³ and R⁴, which may be the same or different, each represent hydrogen, halogen, trifluoromethoxy, or a methyl, ethyl, propyl, or isopropyl group optionally substituted by one or more fluorine atoms, or one of the symbols R², R³ and R⁴ represents methoxy and at least one of the other symbols R², R³ and R⁴ represents halogen, trifluoromethoxy, or a methyl, ethyl, propyl or isopropyl group optionally substituted by one or more fluorine atoms.

2. An imidazole derivative according to claim 1 wherein R¹ represents hydrogen or a straight-chain alkyl group containing from 1 to 8 carbon atoms, R² and R³ are as defined in claim 47 and R⁴ represents hydrogen or chlorine or a trifluoromethyl group, or one of the symbols R², R³ and R⁴ represents a methoxy group and at least one of the other symbols R², R³ and R⁴ represents halogen, a trifluoromethoxy group or a methyl, ethyl, propyl or isopropyl group optionally substituted by one or more fluorine atoms, and with the further proviso that at least one of R², R³ and R⁴ is other than hydrogen or unsubstituted alkyl.

3. An imidazole derivative according to claim 1, wherein R¹ represents hydrogen or a methyl, ethyl, propyl or butyl group, R² and R³ each represents hydrogen or halogen, or a trifluoromethoxy, methyl, ethyl, isopropyl or trifluoromethyl group, and R⁴ represents hydrogen or chlorine or a trifluoromethyl group, or one of the symbols R², R³ and R⁴ represents a methoxy group and at least one of the other symbols R², R³ and R⁴ represents halogen, a trifluoromethoxy group or a methyl, ethyl, propyl or isopropyl group optionally substituted by one or more fluorine atoms, and with the further proviso that at least one of the R², R³ and R⁴ is other than hydrogen or unsubstituted alkyl.

4. An imidazole derivative according to claim 1 which is 1-(4-bromobenzyl)imidazole-N,N'-dimethyl-4,5-dicarboxamide.

5. An imidazole derivative according to claim 1 which is 1-(4-iodobenzyl)imidazole-N,N'-dimethyl-4,5-dicarboxamide.

6. An imidazole derivative according to claim 1 which is 1-(4-trifluoromethoxybenzyl)imidazole-N,N'-dimethyl-4,5-dicarboxamide.

7. An imidazole derivative according to claim 1 which is 1-(4-trifluoromethylbenzyl)imidazole-N,N'-dimethyl-4,5-dicarboxamide.

8. An imidazole derivative according to claim 1 which is 1-[1-(4-trifluoromethylphenyl)ethyl]imidazole-N,N'-dimethyl-4,5-dicarboxamide.

9. An imidazole derivative according to claim 1 which is 1-(3,4-dichlorobenzyl)imidazole-N,N'-dimethyl-4,5-dicarboxamide.

10. An imidazole derivative according to claim 1 which is 1-[1-(3,4-dichlorophenyl)ethyl]imidazole-N,N'-dimethyl-4,5-dicarboxamide.

11. An imidazole derivative according to claim 1 which is 1-(3,4-dibromobenzyl)imidazole-N,N'-dimethyl-4,5-dicarboxamide.

12. An imidazole derivative according to claim 1 which is 1-(4-chloro-3-methylbenzyl)imidazole-N,N'-dimethyl-4,5-dicarboxamide.

13. An imidazole derivative according to claim 1 which is 1-(3,4-diiodobenzyl)imidazole-N,N'-dimethyl-4,5-dicarboxamide.

14. An imidazole derivative according to claim 1 which is 1-(3,4,5-trichlorobenzyl)imidazole-N,N'-dimethyl-4,5-dicarboxamide.

15. An imidazole derivative according to claim 1 which is 1-(4-chlorobenzyl)imidazole-N,N'-dimethyl-4,5-dicarboxamide, 1-[1-(4-chlorophenyl)ethyl]imidazole-N,N'-dimethyl-4,5-dicarboxamide, 1-[1-(4-iodophenyl)ethyl]imidazole-N,N'-dimethyl-4,5-dicarboxamide, 1-[1-(4-trifluoromethoxyphenyl)-ethyl]imidazole-N,N'-dimethyl-4,5-dicarboxamide, 1-[1-(3,4-dichlorophenyl)propyl]imidazole-N,N'-dimethyl-4,5-dicarboxamide, 1-[1-(3,4-dichlorophenyl)butyl]imidazole-N,N'-dimethyl-4,5-dicarboxamide, 1-[1-(3,4-dichlorophenyl)pentyl]imidazole-N,N'-dimethyl-4,5-dicarboxamide, 1-[1-(3,4-dibromophenyl)ethyl]imidazole-N,N'-dimethyl-4,5-dicarboxamide, 1-(4-bromo-3-chlorobenzyl)imidazole-N,N'-dimethyl-4,5-dicarboxamide, 1-(3-chlorobenzyl)imidazole-N,N'-dimethyl-4,5-dicarboxamide, 1-[1-(3-chlorophenyl)ethyl]imidazole-N,N'-dimethyl-4,5-dicarboxamide, 1-(3-fluorobenzyl)imidazole-N,N'-dimethyl-4,5-dicarboxamide, 1-(3-trifluoromethylbenzyl)imidazole-N,N'-dimethyl-4,5-dicarboxamide, 1-[1-(3-trifluoromethylphenyl)-ethyl]imidazole-N,N'-dimethyl-4,5-dicarboxamide, 1-(3,5-dichlorobenzyl)imidazole-N,N'-dimethyl-4,5-dicarboxamide or 1-{1-[3,5-bis(trifluoromethyl)-phenyl]ethyl}imidazole-N,N'-dimethyl-4,5-dicarboxamide.

16. An imidazole derivative according to claim 1 which is 1-(4-fluorobenzyl)imidazole-N,N'-dimethyl-4,5-dicarboxamide, 1-(3-bromobenzyl)imidazole-N,N'-dimethyl-4,5-dicarboxamide, 1-(3-iodobenzyl)imidazole-N,N'-dimethyl-4,5-dicarboxamide, 1-(3-chloro-4-methoxybenzyl)-imidazole-N,N'-dimethyl-4,5-dicarboxamide, 1-(3-bromo-4-methylbenzyl)imidazole-N,N'-dimethyl-4,5-dicarboxamide, 1-(3-chloro-4-methylbenzyl)imidazole-N,N'-dimethyl-4,5-dicarboxamide, or 1-[3,5-bis(trifluoromethyl)benzyl]imidazole-N,N'-dimethyl-4,5-dicarboxamide 1-[1-(3,4-dichlorophenyl)hexyl]imidazole-N,N'-dimethyl-4,5-dicarboxamide, 1-[1-(3,4-dichlorophenyl)heptyl]imidazole-N,N'-dimethyl-4,5-dicarboxamide or 1-[1-(3,4-dichlorophenyl)nonyl]imidazole-N,N'-dimethyl-4,5-dicarboxamide.

17. A herbicidal composition which comprises at least one imidazole derivative as claimed in claim 1 in association with one or more compatible herbicidally-acceptable diluents or carriers, the amount of imidazole derivative in the composition being 0.05 to 90% by weight.

18. A herbicidal composition which comprises at least one imidazole derivative as claimed in any one of claims 4 to 16, 2 or 3 in association with one or more compatible herbicidally-acceptable diluents or carriers, the amount of imidazole derivative in the composition being 0.05 to 90% by weight.

19. A method of controlling the growth of weeds at a locus which comprises applying to the locus a herbicidal composition containing a herbicidally-effective amount of an imidazole derivative as claimed in claim 1.

20. A method according to claim 19 in which weeds controlled by application of the herbicidal composition are one or more of *Avena* spp., *Alopecurus* spp., *Setaria* spp., *Echinochloa* spp., *Eleusine* spp., *Digitaria* spp., *Poa* spp., *Agropyron repens, Agrostris* spp., *Cynodon dactylon, Abutilon theophrasti, Amsinkia intermedia, Anthemis arvensis, Ipomea purpurea, Chenopodium* spp., *Amaranthus* spp., *Polygonum* spp., *Stellaria* spp., *Galium* spp., *Lamium* spp., *Matricaria* spp., *Portulaca* spp., *Sinapis* spp., *Raphanus raphanistrum, Veronica* spp., *Chrysanthemum segetum, Datura stramonium, Descurainea sophia, Emex australis, Erysimum cheiranthoides, Euphorbia helioscopa, Galeopsis tetrahit, Myosotis arvensis, Spergula arvensis, Urtica urens, Viola arvensis, Viola tricolor, Anagallis arvensis, Capsella bursa-pastoris, Papaver rhoeas, Solanum nigrum, Xanthium strumarium, Rumex obtusifolius, Tussilago farfara, Cirsium arvense* and *Cyperus rotundus.*

21. A method according to claim 19 in which weeds controlled by application of the herbicidal composition are one or both of *Monochoria vaginalis* and *Rotala indica.*

22. A method according to claim 19 or 20 in which the herbicidal composition is applied to a crop-growing area at a rate sufficient to control the growth of weeds without causing substantial permanent damage to the crop.

23. A method according to claim 22 in which the imidazole derivative is applied at a rate between 0.25 kg and 20 kg per hectare.

24. A method according to claim 19 for the selective control of the growth of weeds in an area used, or to be used, for growing crops.

25. A method according to claim 24 in which the imidazole derivative is applied at a rate between 0.25 kg and 8.0 kg per hectare.

26. A method according to claim 24 or 25 in which the crop is a graminaceous crop, soya beans, field or dwarf beans, peas, sugar beet, fodder beet, red beet, cotton, peanuts, potatoes, flax, onions, carrots, herbage seed crops or pasture.

27. A method according to claim 26 in which the graminaceous crop is wheat, barley, oats, rye, maize, rice or sorghum.

28. A method according to claim 20 for the selective control of annual broad leaf weeds.

29. A method according to claim 28 in which the herbicidal composition contains as active material 1-(3,4-dichlorobenzyl)imidazole-N,N'-dimethyl-4,5-dicarboxamide, 1-(3,4-dibromobenzyl)imidazole-N,N'-dimethyl-4,5-dicarboxamide or 1-(4-trifluoromethylbenzyl)imidazole-N,N'-dimethyl-4,5-dicarboxamide.

30. A method according to claim 28 in which the weeds are controlled by post-emergence application of the herbicidal composition in a non-directional fashion to an area used for growing graminaceous crops, sugar beet, fodder beet, red beet, onions, herbage seed crops or pasture.

31. A method according to claim 30 in which the graminaceous crop is wheat, barley, oats, rye, maize, rice or sorghum.

32. A method according to claim 28, 29, 30 or 31 in which the imidazole derivative is applied at a rate between 0.25 kg and 4.0 kg per hectare.

33. A method according to claim 19 for the selective control of annual grass and broad leaf weeds.

34. A method according to claim 33 in which the herbicidal composition contains as active material 1-(4-trifluoromethylbenzyl)imidazole-N,N'-dimethyl-4,5-dicarboxamide or 1-[1-(3,4-dichlorophenyl)ethyl]imidazole-N,N'-dimethyl-4,5-dicarboxamide.

35. A method according to claim 33 in which the weeds are controlled by pre-emergence application in a non-directional fashion to an area used for growing graminaceous crops or broad leaf crops before the emergence of the crop above the surface of the soil.

36. A method according to claim 35 in which the graminaceous crop is wheat, barley, oats, rye, maize, rice or sorghum and the broad leaf crop is cotton, soya beans or potatoes.

37. A method according to claim 33, 34, 35 or 36 in which the imidazole derivative is applied at a rate between 0.25 kg and 4.0 kg per hectare.

38. A method according to claim 19 for the control of weeds in established orchards, other tree-growing areas, plantations and shrubberies.

39. A method according to claim 38 in which the other tree-growing areas are forests, woods and parks.

40. A method according to claim 38 in which the herbicidal composition contains as active material 1-(4-trifluoromethylbenzyl)imidazole-N,N'dimethyl-4,5-dicarboxamide, 1-[1-(4-trifluoromethylphenyl)ethyl]imidazole-N,N'-dimethyl-4,5-dicarboxamide or 1-(3,4-dichlorobenzyl)-imidazole-N,N'-dimethyl-4,5-dicarboxamide.

41. A method according to claim 38, 39 or 40 in which the herbicidal composition is applied to the weeds or to the soil in which they are expected to appear at application rates between 0.25 kg and 10.0 kg of active material per hectare.

42. A method according to claim 38, 39 or 40 for the control of annual broad leaf weeds in sugar cane plantations by post-emergence application of the herbicidal composition at a rate between 0.25 kg and 8.0 kg of active material per hectare.

43. A method according to claim 42 in which the rate of application is between 0.25 kg and 4.0 kg of active material per hectare.

44. A method according to claim 19 for the control of the growth of weeds at a locus which is not a crop-growing area which comprises applying to the locus a herbicidally-effective amount of an imidazole derivative in a herbicidal composition as claimed in claim 17.

45. A method according to claim 20 for the control of the growth of weeds at a locus which is not a crop-growing area which comprises applying to the locus a herbicidally-effective amount of an imidazole derivative in a herbicidal composition as claimed in claim 17.

46. A method according to claim 44 or 45 in which the locus is an airfield, industrial site, railway, roadside verge, a river, irrigation or other waterway verge, scrubland or fallow or uncultivated land.

* * * * *

UNITED STATES PATENT AND TRADEMARK OFFICE
CERTIFICATE OF CORRECTION

PATENT NO. : 4,185,992

DATED : January 29, 1980

INVENTOR(S) : James Gilmour et al.

It is certified that error appears in the above—identified patent and that said Letters Patent is hereby corrected as shown below:

Column 5 - line 14, "-" omitted before "4,5-"
line 23, "dimethyl" mis-spelled

Column 9 - lines 15-16 and 20-21 - in each instance for "of the compound of formula XV" read -- of imidazole -4,5-dicarboxylic acid --

Column 18 - line 63, "60°-0°" should be "60° - 80°"

Column 19 - lines 30, 31, 32, 33, 35, 36, 39, 40, 41, 42, 43, 44, 54, 57, 60, 62, 63, 65 - "(+)" should be -- ($\pm$) --

Column 22 - line 66, there should be a square bracket before "3,5-"

Column 23 - lines 14, 24, 25, 32 - "(+)" should be -- ($\pm$) --

Column 26 - line 66, "plating" should be -- planting --

Column 29 (claim 2, line 3) - line 39 - for "8" read -- 4 --

UNITED STATES PATENT AND TRADEMARK OFFICE
CERTIFICATE OF CORRECTION

PATENT NO. : 4,185,992

DATED : January 29, 1980

INVENTOR(S) : James GILMOUR ET AL

It is certified that error appears in the above-identified patent and that said Letters Patent are hereby corrected as shown below:

<u>Column 29</u> (claim 2, line 4) - line 40 -
"47" should be "1"

<u>Column 30</u> (claim 16, line 11) - line 63 -
insert a period (.) after "-4,5-dicarboxamide" and cancel the remainder of the claim.

<u>Column 31</u> (claim 28, line 1) - line 59 -
"20" should be "19"

Signed and Sealed this

Sixteenth Day of December 1980

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,185,992
DATED : January 29, 1980
INVENTOR(S) : James GILMOUR ET AL It is certified that error appears in the above-identified patent and that said Letters Patent are hereby corrected as shown below:

In [75] add the following additional joint inventors:

Leslie Roy HATTON, Harold Wood, England

Edgar William PARNELL, Hornchurch, England

Dennis WARBURTON, Brentwood, England

William George LEEDS, London, England

Column 20 - lines 1, 16, 62 and 63 -
"(+)" should be -- ($\pm$) --

Column 21 - line 15, "(+)" should be -- ($\pm$) --

Signed and Sealed this

Third Day of March 1981

[SEAL]

Attest:

RENE D. TEGTMEYER

Attesting Officer   Acting Commissioner of Patents and Trademarks